(12) United States Patent
Sassenfeld et al.

(10) Patent No.: US 7,083,948 B1
(45) Date of Patent: Aug. 1, 2006

(54) POLYPEPTIDE PURIFICATION REAGENTS AND METHODS FOR THEIR USE

(75) Inventors: Helmut M. Sassenfeld, Bainbridge Island, WA (US); Rebecca E. McCoy, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 10/740,880

(22) Filed: Dec. 19, 2003

Related U.S. Application Data

(60) Provisional application No. 60/436,362, filed on Dec. 24, 2002.

(51) Int. Cl.
C12P 21/06 (2006.01)

(52) U.S. Cl. ............... 435/69.1; 530/350; 530/412

(58) Field of Classification Search ............. 435/69.1; 530/350, 412
See application file for complete search history.

(56) References Cited

U.S. PATENT DOCUMENTS

| | | | |
|---|---|---|---|
| 4,609,707 A | 9/1986 | Nowinski et al. | |
| 5,998,588 A | 12/1999 | Hoffman et al. | |
| 6,207,446 B1 * | 3/2001 | Szostak et al. | 435/287.2 |
| 6,258,275 B1 | 7/2001 | Freitag et al. | |
| 6,326,155 B1 | 12/2001 | Maclennan et al. | |
| 2002/0019517 A1 | 2/2002 | Koide | |
| 2002/0137891 A1 | 9/2002 | Hill et al. | |

FOREIGN PATENT DOCUMENTS

| | | |
|---|---|---|
| EP | 0221175 B1 | 2/1991 |
| WO | WO 00/34784 | 6/2000 |
| WO | WO 01/02440 A1 | 1/2001 |

OTHER PUBLICATIONS

Irwin et al., Affinity precipitation: a novel approach to protein purification, Essays Biochem. 1995;29:137-56.*

Galaev, I. Yu., "New Methods of Protein Purification. Affinity Ultrafiltration," *Biochem.* (Moscow) 64(8):849-856, 1999 (translated from *Biokhimiya* (64(8):1013-1021).

Galaev I. and Mattiasson B., "'Smart' polymers and what they could do in biotechnology and medicine," *TIBTECH* 17:335-340, 1999.

Hoffman et al., "Really smart bioconjugates of smart polymers and receptor proteins," Founder's Award, Sixth World Biomaterials Congress 2000, Kamuela, HI, May 15-20, *J. Biomed Mater Res.* 52:577-586, 2000.

Irwin J. and Tipton K., "Affinity Precipitation Methods," *Methods in Molecular Biology*, Ed: S. Doonan, Totowa, NJ: Humana Press Inc., vol. 59:217-238.

Larsson, P. and Mosbach, K., "Affinity Precipitation of Enzymes," *FEBS Letters*:98(2): 333-338, 1979.

Hilbrig and Freitag, "Protein purification by affinity precipitation," *J Chromatogr B 790*:79-90, 2003.

Labrou and Clonis, "The affinity technology in downstream processing," *J Biotechnol 36*:95-119, 1994.

Roque et al., "Antibodies and genetically engineered related molecules: production and purification," *Biotechnol Prog 20*:639-654, 2004.

* cited by examiner

*Primary Examiner*—Jon Weber
*Assistant Examiner*—Robert B. Mondesi
(74) *Attorney, Agent, or Firm*—Rosemary Sweeney

(57) ABSTRACT

The present invention provides polypeptide purification reagents that are, themselves, proteins and methods for using these to purify almost any protein of interest. A polypeptide purification reagent comprises a polypeptide domain that can bind to a protein of interest and a polypeptide domain that confers a propensity to precipitate under conditions where the vast majority of proteins will not precipitate. In addition or as an alternative, a polypeptide purification reagent can comprise amino acid sequences that confer an ability to partition into a phase in a liquid—liquid phase system that the majority of proteins do not partition into. Methods for purifying a protein of interest using such polypeptide purification reagents are also provided. The methods include forming a precipitate comprising the polypeptide purification reagent and the protein of interest under conditions in which the vast majority of proteins do not precipitate and in which the biological activities of both proteins are substantially preserved. The methods further include an optional repurification by one or more reprecipitation steps or by affinity chromatography. In addition or as an alternative, the methods include recovering the protein of interest bound to the polypeptide purification reagent in a phase of a liquid—liquid phase system. The methods further include separating the protein of interest from the polypeptide purification reagent.

24 Claims, 11 Drawing Sheets

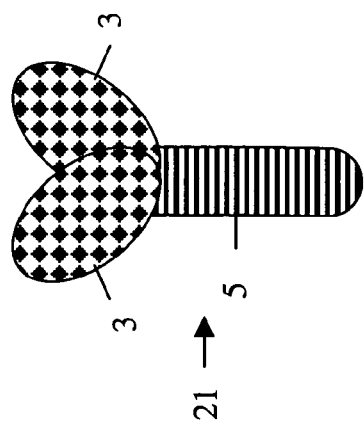
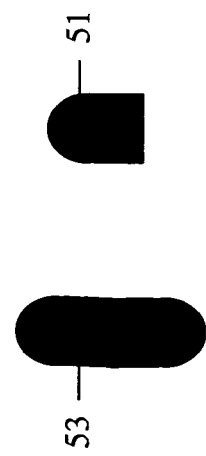
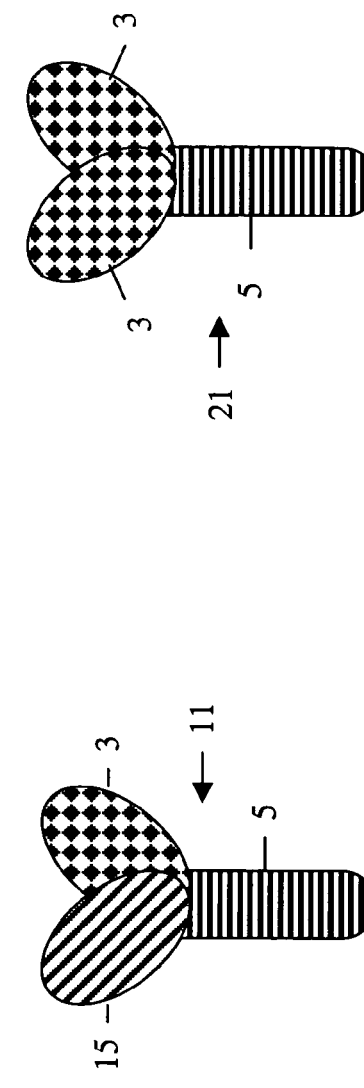
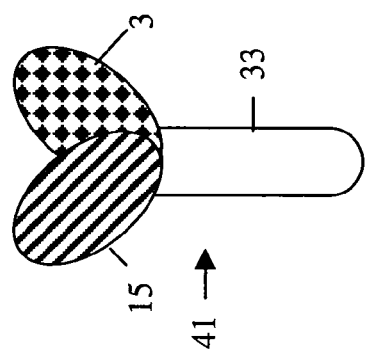
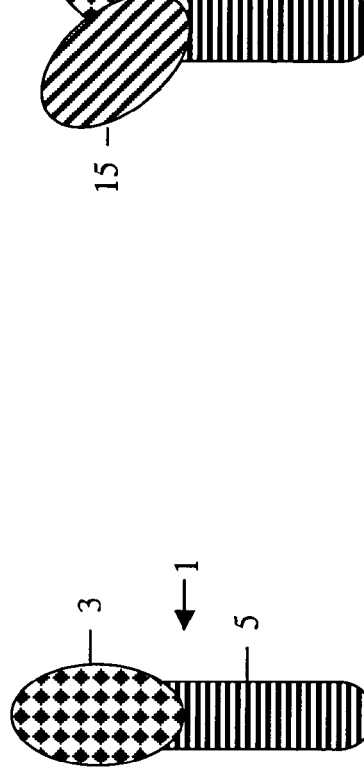
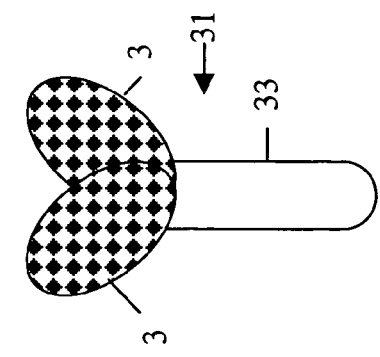

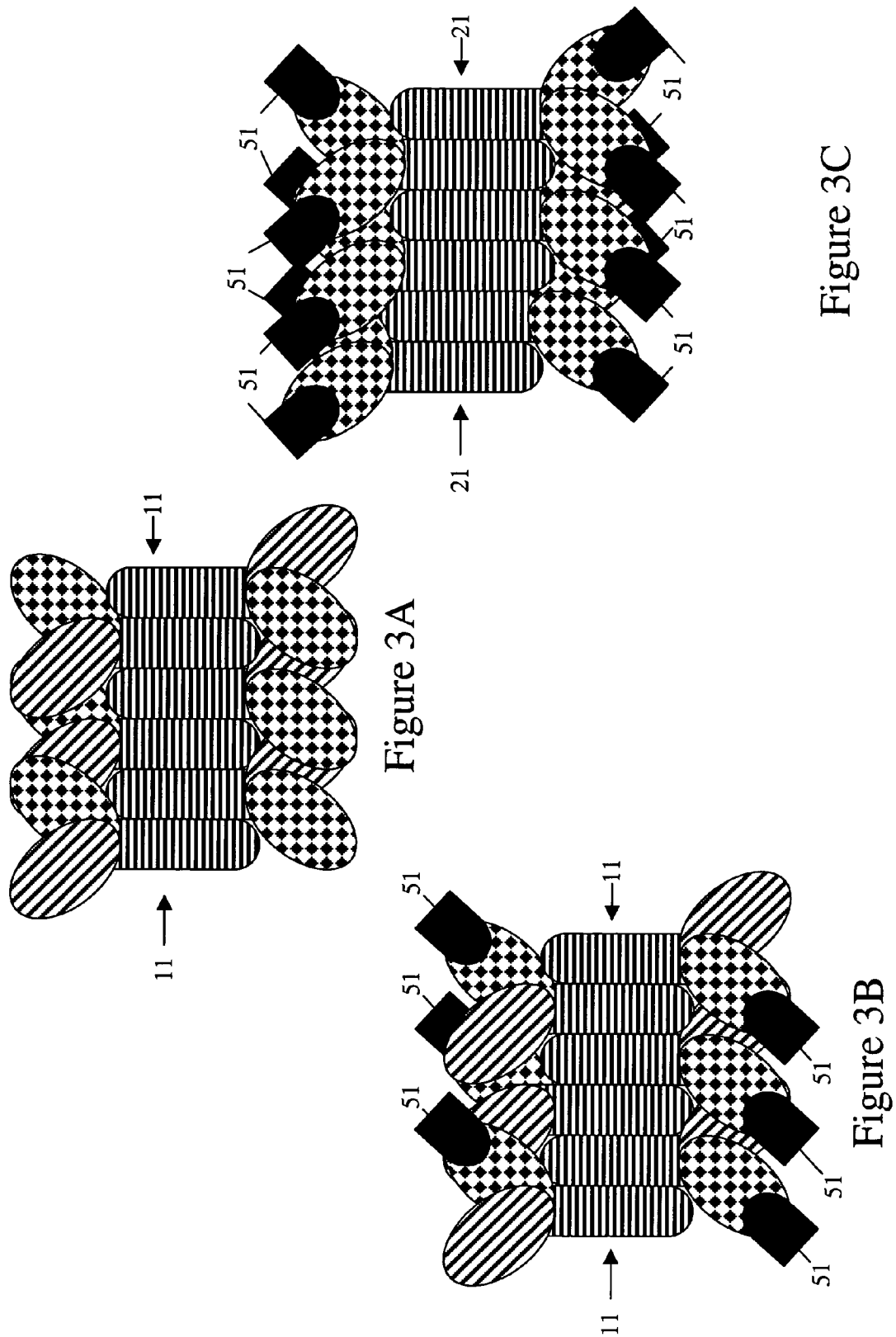

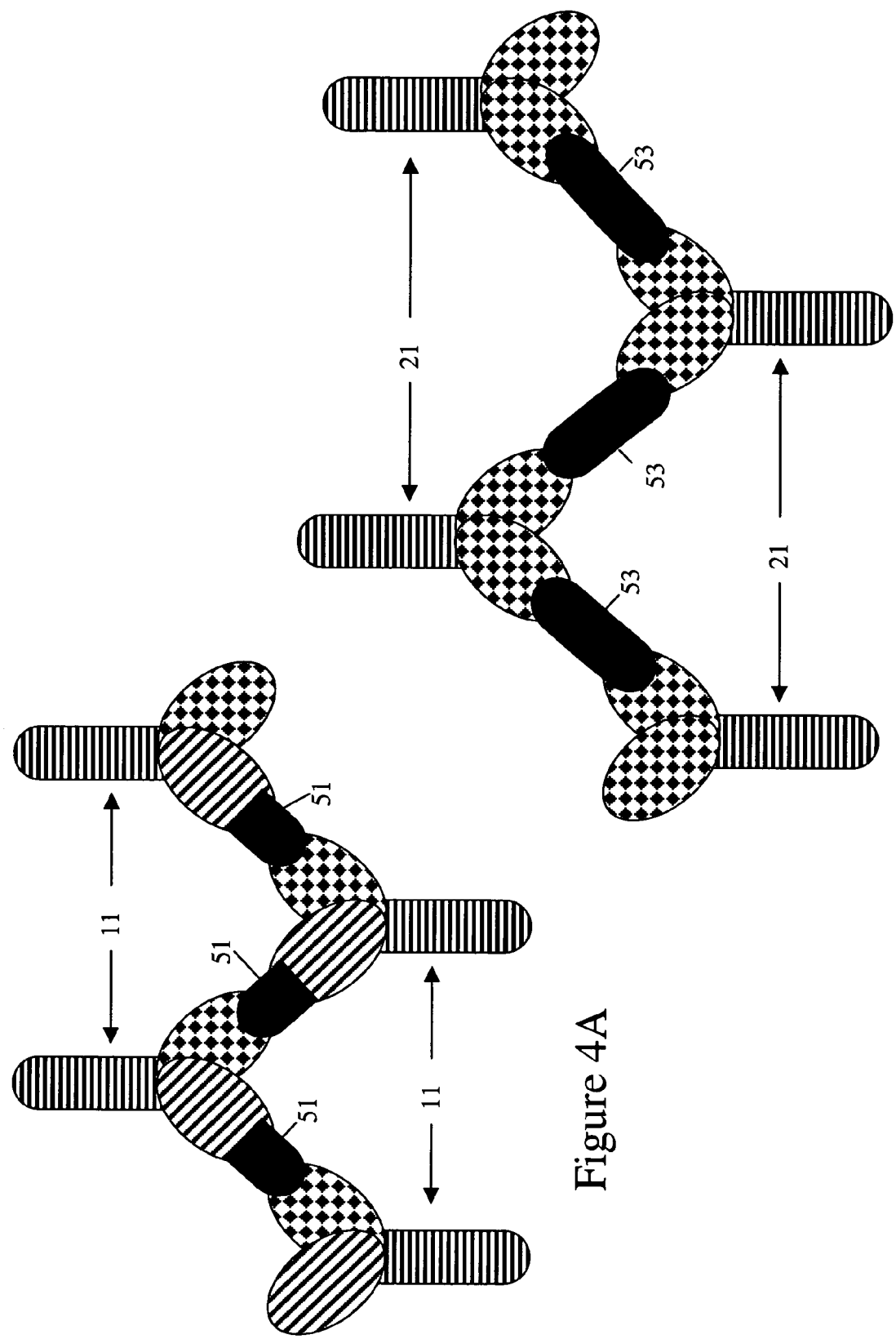

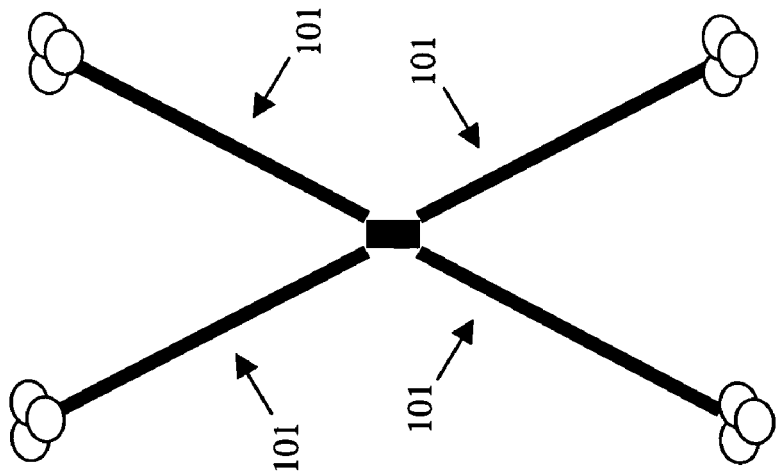
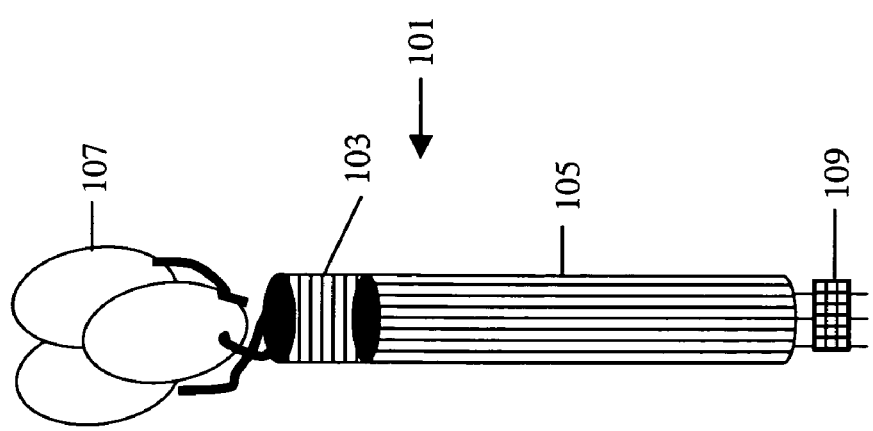
Figure 5B
Figure 5A

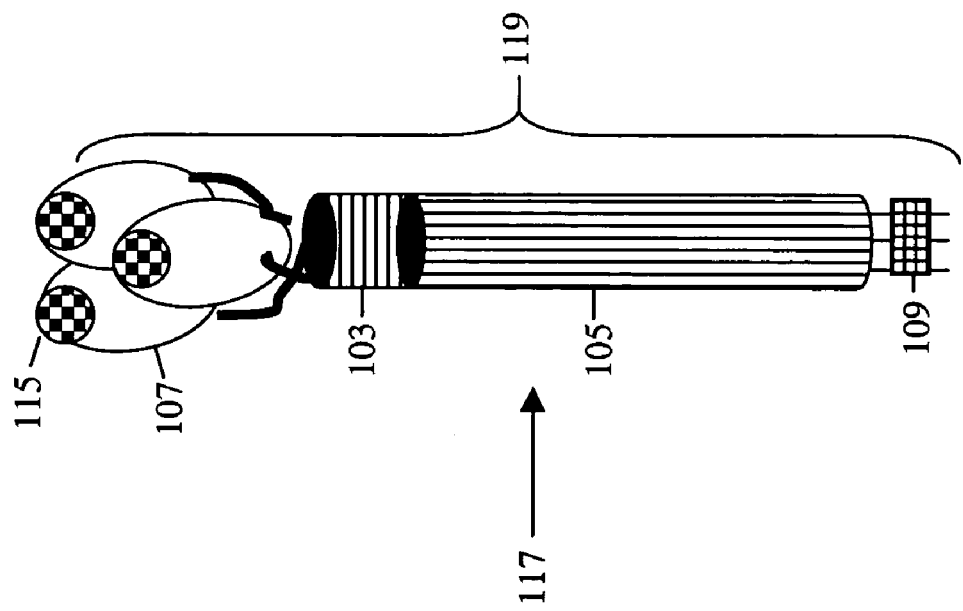
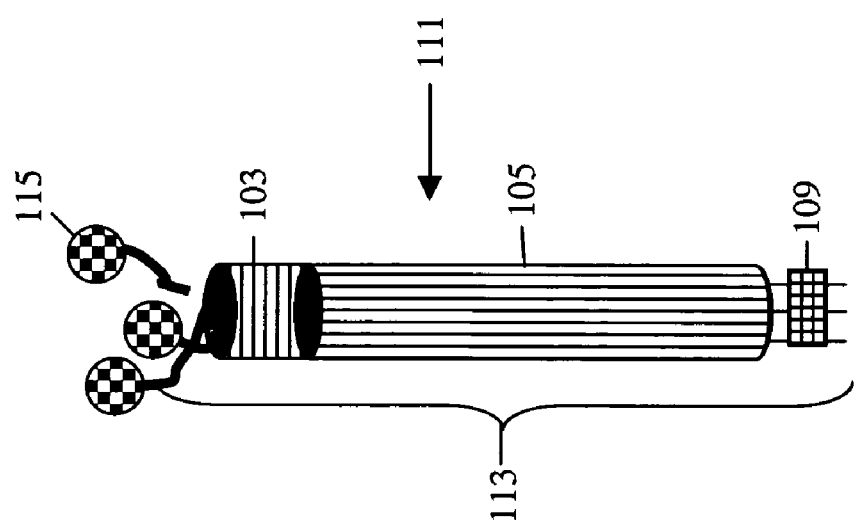

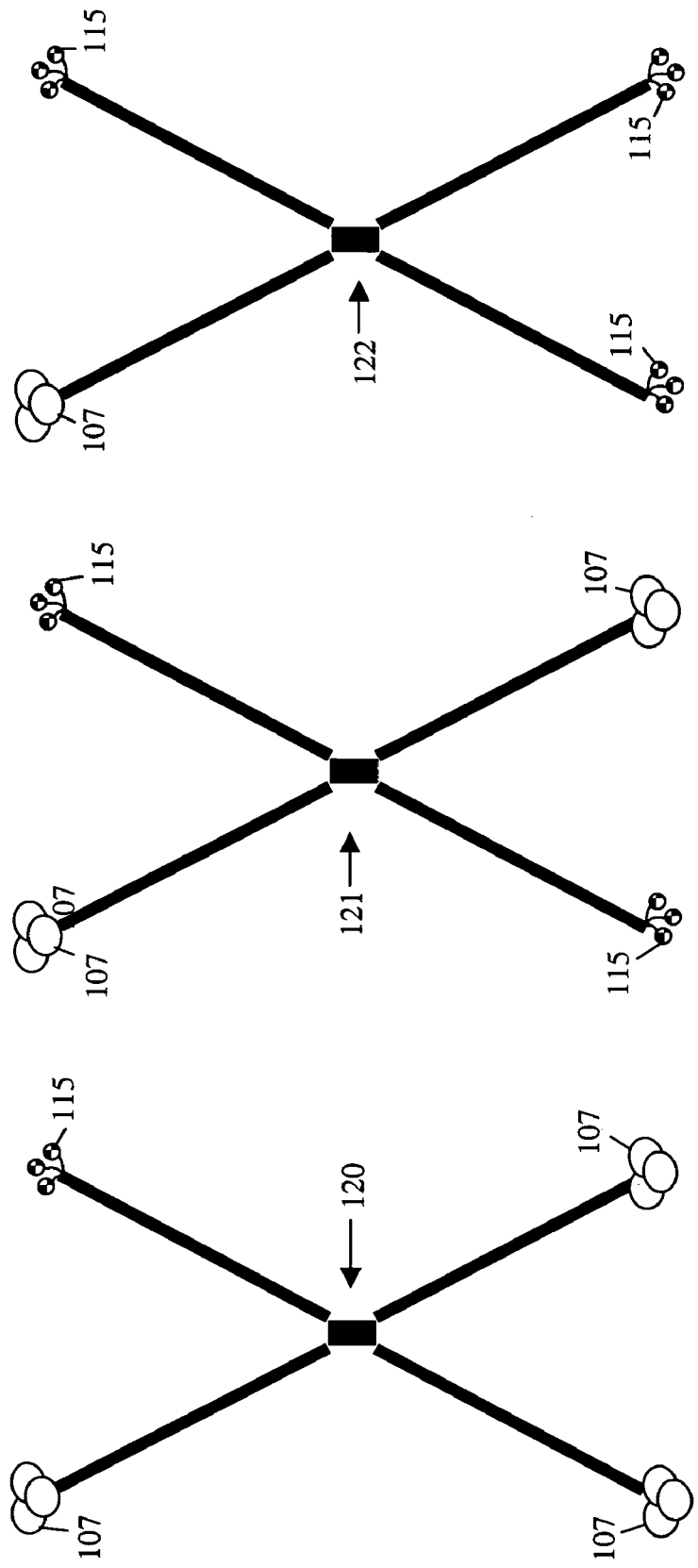

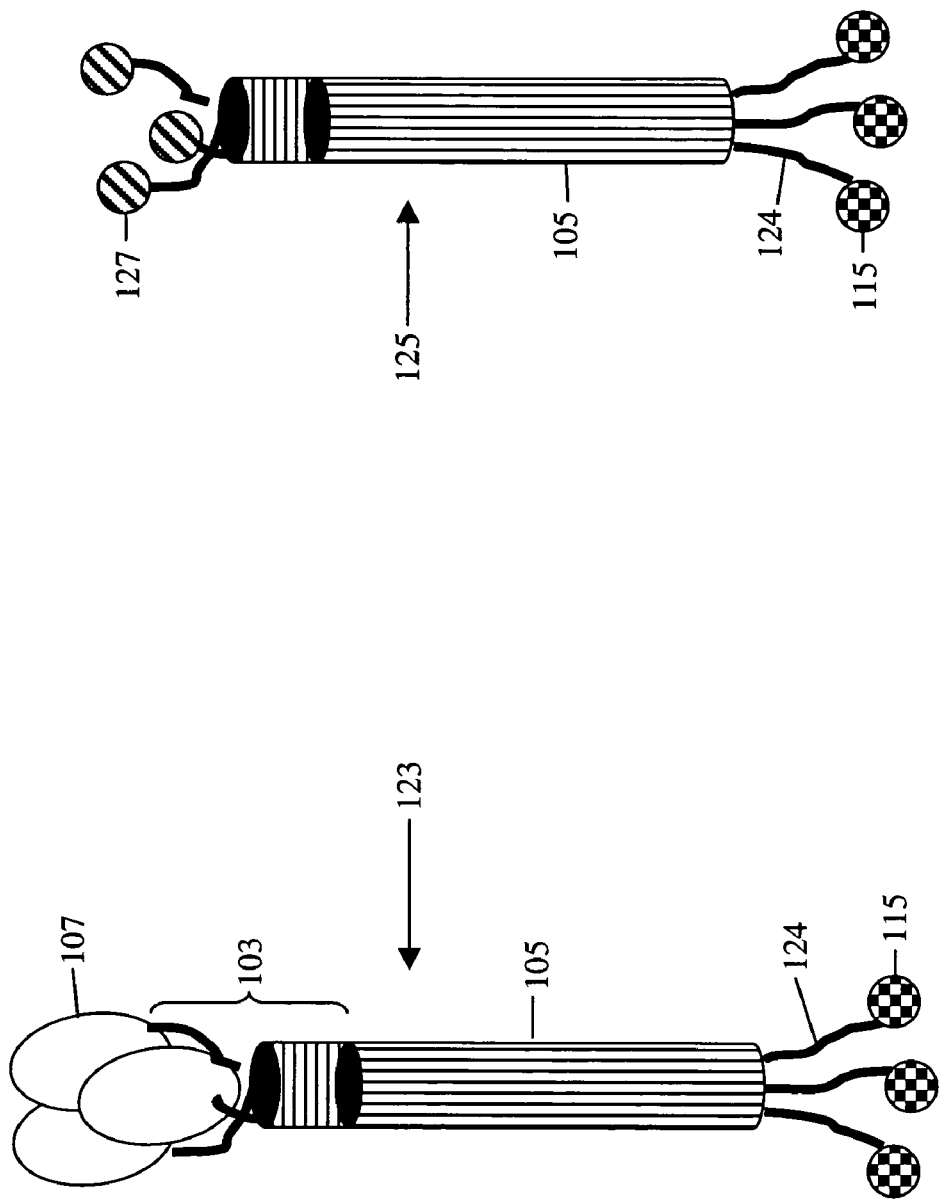

SEQUENCE LISTING

<160> NUMBER OF SEQ ID NOS: 8

<210> SEQ ID NO 1
<211> LENGTH: 5
<212> TYPE: PRT

```
<213> ORGANISM: Artificial
<220> FEATURE:
<223> OTHER INFORMATION: Peptide linker

<400> SEQUENCE: 1

Gly Gly Gly Gly Ser
1               5

<210> SEQ ID NO 2
<211> LENGTH: 5
<212> TYPE: PRT
<213> ORGANISM: Artificial
<220> FEATURE:
<223> OTHER INFORMATION: Peptide linker
<220> FEATURE:
<221> NAME/KEY: MISC_FEATURE
<222> LOCATION: (1)..(5)
<223> OTHER INFORMATION: this sequence comprises 1 to N contiguous
      repeats of amino acids 1 through 5 wherein N is a positive integer

<400> SEQUENCE: 2

Gly Gly Gly Gly Ser
1               5

<210> SEQ ID NO 3
<211> LENGTH: 12
<212> TYPE: PRT
<213> ORGANISM: Artificial
<220> FEATURE:
<223> OTHER INFORMATION: Peptide linker

<400> SEQUENCE: 3

Gly Lys Ser Ser Gly Ser Gly Ser Glu Ser Lys Ser
1               5                   10

<210> SEQ ID NO 4
<211> LENGTH: 14
<212> TYPE: PRT
<213> ORGANISM: Artificial
<220> FEATURE:
<223> OTHER INFORMATION: Peptide linker

<400> SEQUENCE: 4

Gly Ser Thr Ser Gly Ser Gly Lys Ser Ser Glu Gly Lys Gly
1               5                   10

<210> SEQ ID NO 5
<211> LENGTH: 18
<212> TYPE: PRT
<213> ORGANISM: Artificial
<220> FEATURE:
<223> OTHER INFORMATION: Peptide linker

<400> SEQUENCE: 5

Gly Ser Thr Ser Gly Ser Gly Lys Ser Ser Glu Gly Ser Gly Ser Thr
1               5                   10                  15

Lys Gly

<210> SEQ ID NO 6
<211> LENGTH: 14
<212> TYPE: PRT
<213> ORGANISM: Artificial
<220> FEATURE:
<223> OTHER INFORMATION: Peptide linker

<400> SEQUENCE: 6

Gly Ser Thr Ser Gly Ser Gly Lys Ser Ser Glu Gly Lys Gly
```

```
-continued 1               5               10

<210> SEQ ID NO 7
<211> LENGTH: 18
<212> TYPE: PRT
<213> ORGANISM: Artificial
<220> FEATURE:
<223> OTHER INFORMATION: Peptide linker

<400> SEQUENCE: 7

Gly Ser Thr Ser Gly Ser Gly Lys Pro Gly Ser Gly Glu Gly Ser Thr
1               5                   10                  15

Lys Gly

<210> SEQ ID NO 8
<211> LENGTH: 14
<212> TYPE: PRT
<213> ORGANISM: Artificial
<220> FEATURE:
<223> OTHER INFORMATION: Peptide linker

<400> SEQUENCE: 8

Glu Gly Lys Ser Ser Gly Ser Gly Ser Glu Ser Lys Glu Phe
1               5                   10
```

POLYPEPTIDE PURIFICATION REAGENTS AND METHODS FOR THEIR USE

This application claims benefit of U.S. Provisional Application No. 60/436,362, filed Dec. 24, 2002, which is incorporated herein in its entirety.

FIELD OF INVENTION

The present invention relates to compositions of matter to be used for protein purification and methods of making and using such compositions.

BACKGROUND

Protein purification, especially at industrial scales, can be laborious and expensive. Although the use of column chromatography to purify a protein is effective, it contributes substantially to the labor and expense of producing a pure protein, in part because of the large volumes of solutions necessary for column chromatography. Thus, methods of purification that do not depend on column chromatography and that can be performed in a low volume are commercially advantageous.

Some methods of protein purification require the modification of the protein to be purified, for example by adding a covalently-linked protein tag, to facilitate purification. In some situations, particularly for pharmaceutical use, such modifications may need to be removed subsequent to purification and prior to use because of unwanted effects on the final protein product.

It would therefore be desirable to develop methods for protein purification applicable to a wide variety of proteins that can minimize or eliminate both the need for column chromatography and the need to modify the protein being purified.

SUMMARY

The invention makes novel use of the various available techniques to select protein domains with virtually any desired property. In particular, the instant invention relates to the design of polypeptide purification reagents, which can themselves be proteins, and methods for using them to purify virtually any protein desired. The polypeptide purification reagents comprise polypeptide domains that can bind specifically to proteins of interest and polypeptide domains that allow the selective precipitation of the polypeptide purification reagent or its recovery in a phase of a liquid—liquid phase separation system. Thus, the protein of interest, bound to the polypeptide purification reagent, can be easily recovered even from large volumes of starting material. Repeated cycles of such purification can enhance the purity of the protein of interest. The invention further envisions separation and recovery of both the protein of interest and the polypeptide purification reagent, which can be reused. Thus, the invention enables a high throughput purification in a relatively small final volume, which is likely to result in cost savings.

In one aspect, the invention comprises a method of using a recombinant, non-antibody polypeptide purification reagent for purifying a protein of interest by (1) combining the recombinant, non-antibody polypeptide purification reagent with the protein of interest, wherein all or part of the polypeptide purification reagent is the product of an in vitro selection for binding to the protein of interest, (2) adjusting conditions such that the polypeptide purification reagent can bind to the protein of interest, (3) adjusting conditions such that the polypeptide purification reagent, when bound to the protein of interest, can form a precipitate, wherein formation of the precipitate does not irreversibly alter the functional properties of the protein of interest or the polypeptide purification reagent, and (4) recovering the polypeptide purification reagent bound to the protein of interest as a precipitate. This method can further comprise resuspending the precipitate under conditions such that the protein of interest does not bind to the polypeptide purification reagent and the polypeptide purification reagent does not form a precipitate and separating the protein of interest from the polypeptide purification reagent by subjecting the resuspended precipitate to affinity chromatography using an affinity reagent that specifically binds to the polypeptide purification reagent. Alternatively, the method can further comprise (1) resuspending the precipitate under conditions such that the protein of interest does not bind to the polypeptide purification reagent and the polypeptide purification reagent does not form a precipitate, (2) adjusting the conditions such that the polypeptide purification reagent forms a precipitate and the protein of interest does not bind to the polypeptide purification reagent, and (3) separating the precipitate comprising the polypeptide purification reagent from the solution comprising the protein of interest. The protein of interest may comprise an Fc portion of an antibody, and the polypeptide purification reagent may comprise all or part of a C-type lectin. The precipitate may or may not be a crystal. A molecule of the polypeptide purification reagent may be able to bind to another molecule of the polypeptide purification reagent. The protein of interest may comprise the Fc portion of an antibody, and the polypeptide purification reagent may comprise at least two binding domains comprising all or part of Protein A. The polypeptide purification reagent may comprise at least two binding domains, each of which may bind to different epitopes on the protein of interest.

The invention provides a method for purifying a protein of interest comprising combining a polypeptide purification reagent with the protein of interest under conditions such that a precipitate lacking a regular, crystalline structure comprising the polypeptide purification reagent and the protein of interest is formed and recovering the polypeptide purification reagent bound to the protein of interest as a precipitate. Further, the precipitate can be resuspended under conditions such that the polypeptide purification reagent does not bind to the protein of interest, the polypeptide purification reagent can be separated from the protein of interest, and both the polypeptide purification reagent and the protein of interest can be recovered. The protein of interest can comprise an $F_C$ portion of an antibody, and the polypeptide purification reagent can comprise at least two binding domains, which may comprise all or part of Protein A, that can bind to an $F_C$ portion of an antibody.

In another aspect, the invention provides a method of purifying a protein of interest comprising (1) combining a polypeptide purification reagent with the protein of interest, wherein the polypeptide purification reagent comprises a binding domain and a distinct scaffold domain, wherein the scaffold domain comprises an amino acid sequence conferring a propensity to form a precipitate, (2) adjusting conditions such that the polypeptide purification reagent can bind to the protein of interest and such that the polypeptide purification reagent, when bound to the protein of interest, can form a precipitate, and (3) recovering the polypeptide purification reagent bound to the protein of interest as a precipitate. The protein of interest may comprise all or part of antibody or a substantially similar protein. The binding domain in the polypeptide purification reagent may have been selected in vitro to bind to the protein of interest.

The precipitate can be resuspended under conditions such that the polypeptide purification reagent does not bind to the protein of interest and does not form a precipitate. The conditions can then be adjusted such that the polypeptide purification reagent does not bind to the protein of interest and does form a precipitate. The precipitate can be separated from the solution.

In another aspect, the invention encompasses a polypeptide purification reagent comprising all or part of a C-type lectin and a binding domain that can specifically and reversibly bind to a protein of interest, wherein the binding domain does not comprise a variable antibody immunoglobulin domain. The protein of interest may comprise all or part of an antibody or a substantially similar protein. In still another aspect, such a polypeptide purification reagent can be used to perform a method comprising the following steps: (1) combining the polypeptide purification reagent with the protein of interest; (2) adjusting conditions such that the polypeptide purification reagent can bind to the protein of interest; (3) adjusting conditions such that the polypeptide purification reagent, when bound to the protein of interest, forms a precipitate; and (4) recovering the polypeptide purification reagent bound to the protein of interest as a precipitate. This method can further comprise separating the polypeptide purification reagent from the protein of interest and recovering both the polypeptide purification reagent and the protein of interest.

In still another aspect, the invention encompasses a polypeptide purification reagent for purifying a protein of interest comprising at least one binding domain that can specifically and reversibly bind to the protein of interest and at least one scaffold domain that is fused to or part of the binding domain(s), wherein the scaffold domain comprises amino acid sequences conferring a propensity to form a precipitate. The binding domain(s) may be selected in vitro to bind to the protein of interest, and a portion of the polypeptide purification reagent may be selected in vitro to bind to a portion of the polypeptide purification reagent. Such a polypeptide purification reagent can be used to purify a protein of interest using a method comprising the following steps: (1) combining the polypeptide purification reagent with the protein of interest; (2) adjusting conditions such that the polypeptide purification reagent can bind to the protein of interest; (3) adjusting conditions such that the polypeptide purification reagent, when bound to the protein of interest, can form a precipitate; and (4) recovering the polypeptide purification reagent bound to the protein of interest as a precipitate. A polypeptide purification reagent that can bind to itself can be used in a method for purifying a protein of interest comprising the following steps: (1) combining the polypeptide purification reagent with the protein of interest; (2) adjusting conditions such that the polypeptide purification reagent can bind to the protein of interest; (3) adjusting conditions such that the polypeptide purification reagent can form a precipitable polymer by binding to itself; (4) recovering the polypeptide purification reagent bound to the protein of interest as a precipitate.

In another aspect, the invention encompasses a polypeptide purification reagent for purifying a protein of interest comprising at least one scaffold domain and at least two binding domains fused to the scaffold domain, wherein each of the two binding domains can specifically and reversibly bind to an epitope on the protein of interest, wherein binding of plural molecules of the protein of interest by plural molecules of the polypeptide purification reagent results in the reversible formation of a precipitable polymer, and wherein the polypeptide purification reagent is a recombinant, non-antibody protein. The polypeptide purification reagent may comprise at least one protein tag.

In still another embodiment, the invention includes a method of making a polypeptide purification reagent for purifying a protein of interest comprising the following steps: (1) inserting nucleotide sequences encoding the polypeptide purification reagent, which comprises nucleotide sequences encoding at least one non-antibody scaffold domain fused to nucleotide sequences encoding at least one non-antibody binding domain, into a recombinant vector designed to allow expression of the inserted sequences; (2) introducing the recombinant vector with the inserted nucleotide sequences into cells that can express the inserted nucleotide sequences; (3) culturing the cells under conditions in which the inserted sequences are expressed; and (4) recovering the polypeptide purification reagent from the cultured cells. In this method, each binding domain can specifically and reversibly bind to an epitope on the protein of interest, and the polypeptide purification reagent and the protein of interest can form a precipitate when bound to each other. The polypeptide purification reagent may be able to bind to at least two different epitopes on the protein of interest and may comprise amino acids conferring a propensity to form a precipitate.

In a further embodiment, the invention includes a method for purifying a protein of interest comprising the following steps: (1) combining such a polypeptide purification reagent with the protein of interest under conditions such that at least two binding domains can specifically and reversibly bind to the protein of interest, thereby creating a precipitable polymer comprising the polypeptide purification reagent and the protein of interest, wherein the precipitable polymer can form a precipitate; (2) separating the precipitate, which comprises the precipitable polymer, from the solution; (3) resuspending the precipitate under conditions such that the protein of interest does not bind to the polypeptide purification reagent; and (4) separating the protein of interest from the polypeptide purification reagent. Separating the protein of interest from the polypeptide purification reagent may comprise the following steps: (1) combining the resuspended precipitable polymer with an affinity reagent affixed to a solid support that binds to the polypeptide purification reagent under conditions that allow this binding; (2) recovering molecules that do not bind to the affinity reagent, which comprise the protein of interest; and (3) eluting and recovering molecules that do bind to the affinity reagent, which comprise the polypeptide purification reagent.

An alternative method for purifying a protein of interest comprises the following steps: (1) combining a polypeptide purification reagent, which has at least two binding domains and has a propensity to precipitate, with the protein of interest under conditions such that at least two binding domains can specifically bind to the protein of interest, thereby forming a precipitable polymer that can form a precipitate comprising the polypeptide purification reagent and the protein of interest; (2) separating the precipitate comprising the precipitable polymer from the solution; (3) resuspending the precipitable polymer under conditions such that not all of the binding domains of the polypeptide purification reagent can bind to the protein of interest and at least one of the binding domains can bind to the protein of interest, thereby dissociating the precipitable polymer; (4) adjusting the conditions such that the polypeptide purification reagent can form a precipitate and at least one of the binding domains can bind to the protein of interest; (5) separating the precipitate from the solution; (6) resuspending the precipitate in solution under conditions such that none of the binding domains of the polypeptide purification reagent can bind to the protein of interest; and (7) separating the polypeptide purification reagent from the protein of interest.

In another embodiment, the invention provides a polypeptide purification reagent comprising at least three identical, covalently linked polypeptides, each of which can bind to an $F_C$ portion of an antibody, wherein multiple molecules of the polypeptide purification reagent are soluble in an aqueous solution when not bound to multiple molecules of a protein comprising an $F_C$ portion of an antibody. The identical polypeptides can be all or part of Protein A or can be a polypeptide selected in vitro to bind to an $F_C$ portion of an antibody. The identical polypeptides can be covalently linked via peptide or non-peptide linkers. Such polypeptide purification reagents can be used to purify a protein of interest by a method comprising the steps of: (a) combining the polypeptide purification reagent with the protein of interest under conditions such that a precipitable polymer comprising the polypeptide purification reagent and the protein of interest is formed, wherein the protein of interest comprises an $F_C$ portion of an antibody; and (b) recovering the polypeptide purification reagent bound to the protein of interest as a precipitate. This method may further comprise steps of (a) separating the polypeptide purification reagent from the protein of interest, and (b) recovering both the polypeptide purification reagent and the protein of interest.

In still another aspect, the invention includes a polypeptide purification reagent, optionally a recombinant polypeptide purification reagent, comprising at least 2 binding domains comprising of all or part of Protein A and/or comprising at least one scaffold domain comprising all or part of a C type lectin and at least one binding domain.

In still another aspect, the invention encompasses a recombinant, polypeptide purification reagent for purifying a protein of interest comprising a means for specifically and reversibly binding the protein of interest, a means for forming a precipitate when bound to the protein of interest, and a means for separating the protein of interest from the polypeptide purification reagent. Such a polypeptide purification reagent does not comprise a variable antibody immunoglobulin domain.

In a final aspect, the invention encompasses a substantially purified form of a protein of interest comprising detectable traces of a polypeptide purification reagent.

BRIEF DESCRIPTION OF THE FIGURES

FIG. 1A depicts an embodiment of a polypeptide purification reagent 1, comprising a single binding domain 3 that can bind a protein of interest and a single scaffold domain 5 that confers a propensity to precipitate.

FIG. 1B depicts an embodiment of a polypeptide purification reagent 11, comprising two binding domains 3 and 15 that can bind to different epitopes on a protein of interest and a single scaffold domain 5 that confers a propensity to precipitate.

FIG. 1C depicts an embodiment of a polypeptide purification reagent 21, comprising two binding domains 3 and 3 that can bind to identical epitopes on a protein of interest and a single scaffold domain 5 that confers a propensity to precipitate.

FIG. 1D depicts an embodiment of a polypeptide purification reagent 31, comprising two binding domains 3 and 3 that can bind to identical epitopes on a protein of interest and a single scaffold domain 33 that does not confer a propensity to precipitate.

FIG. 1E depicts an embodiment of a polypeptide purification reagent 41, comprising two binding domains 3 and 15 that can bind to different epitopes on a protein of interest and a single scaffold domain 33 that does not confer a propensity to precipitate.

FIG. 1F depicts monomeric 51 and dimeric 53 embodiments of a protein of interest.

FIG. 3A represents the crystallization of polypeptide purification reagent 11 (FIG. 1B) when it is not bound to protein of interest.

FIG. 3B represents the crystallization of polypeptide purification reagent 11 (FIG. 1B) when it is bound to protein of interest 51 (FIG. 1F).

FIG. 3C represents the crystallization of polypeptide purification reagent 21 (FIG. 1C) when it is bound to protein of interest 51 (FIG. 1F).

FIG. 4A depicts a precipitable polymer comprising polypeptide purification reagent 11 (FIG. 1B) and protein of interest 51 (FIG. 1F).

FIG. 4B depicts a precipitable polymer comprising polypeptide purification reagent 21 (FIG. 1C) and protein of interest 53 (FIG. 1F).

FIG. 5A depicts a C-type lectin trimer 101 including a carbohydrate recognition domain (CRD) 107, a neck region 103, a collagenous region 105, and an amino terminal domain 109.

FIG. 5B depicts a C-type lectin dodecamer comprising four C-type lectin trimers 101 (FIG. 5A) linked at their amino terminal regions.

FIG. 6A depicts a trimeric polypeptide purification reagent 111 in which the carbohydrate recognition domain (CRD) 107 (FIG. 5A) of a C-type lectin is replaced by a binding domain 115 that can bind to a protein of interest.

FIG. 6B depicts a trimeric polypeptide purification reagent 117 in which a binding domain 115 that can bind to a protein of interest has been added to a C-type lectin that comprises all or part of a CRD 107 (FIG. 5A).

FIG. 7A depicts a polypeptide purification reagent 120 that is a dodecamer comprising three C-type lectin trimers 101 (FIG. 5A) plus one trimeric polypeptide purification reagent 111 or 117 (FIG. 6A or 6B).

FIG. 7B depicts a polypeptide purification reagent 121 that is a dodecamer comprising two C-type lectin trimers 101 (FIG. 5A) plus two trimeric polypeptide purification reagents 111 or 117 (FIG. 6A or 6B).

FIG. 7C depicts a polypeptide purification reagent 122 that is a dodecamer comprising one C-type lectin trimer 101 (FIG. 5A) plus three trimeric polypeptide purification reagents 111 or 117 (FIG. 6A or 6B).

FIG. 8 depicts a trimeric polypeptide purification reagent 123 in which a binding domain 115 that can bind to a protein of interest and a peptide linker 124 replace an amino terminal domain 109 (FIG. 5A) of a C-type lectin.

FIG. 9 depicts a trimeric polypeptide purification reagent 125 in which a binding domain 115 that can bind to a protein of interest and a peptide linker 124 replace an amino terminal domain 109 (FIG. 5A) of a C-type lectin and a self-binding domain 127 replaces a CRD 107 (FIG. 5A).

DETAILED DESCRIPTION OF THE INVENTION

Definitions

Figure 2B:
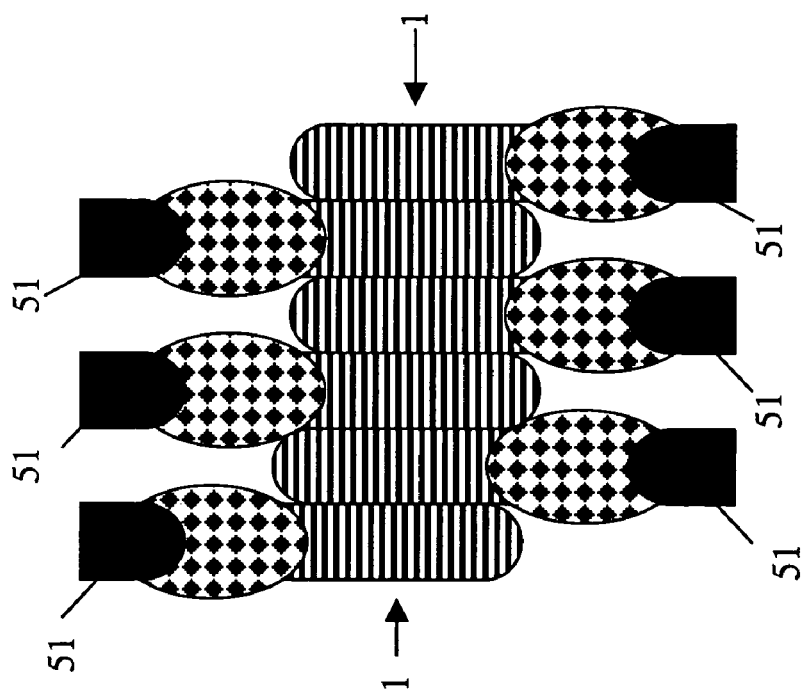
FIG. 2B represents the crystallization of polypeptide purification reagent 1 (FIG. 1A) when it is bound to protein of interest 51 (FIG. 1F).

Affinity reagent: An affinity reagent is a molecule that specifically and reversibly binds to a polypeptide. Affinity reagents may be attached to a solid support for affinity chromatography, which uses the specific, reversible interactions between an affinity reagent and a protein, rather than the general properties of a protein, such as isoelectric point, hydrophobicity, or size, to effect chromatographic separation. See e.g. Ostrove (1990), in Guide to Protein Purification, Methods in Enzymology 182:357–379.

Antibody: An antibody is a protein or complex of proteins, each of which comprises at least one variable antibody immunoglobulin domain and at least one constant antibody immunoglobulin domain. Antibodies may be single chain antibodies, dimeric antibodies, or some higher order complex of proteins including, but not limited to, heterodimeric antibodies.

Binding domain: A binding domain is a polypeptide that can specifically and reversibly bind to a protein of interest. It is to be understood that any particular binding domain binds to a specific epitope within a protein of interest.

C-type lectin: C-type lectins include SP-D, SP-A, conglutinin, Collectin-43, MBP, C1q A-chain, C1q B-chain, C1q C-chain, or substantially similar proteins. See e.g. Hoppe and Reid (1994), Structure 2:1129–1133.

Constant antibody immunoglobulin domain: A constant antibody immunoglobulin domain is an immunoglobulin domain that is identical to or substantially similar to a $C_L$, $C_H1$, $C_H2$, $C_H3$, or $C_H4$, domain of human or animal origin. See e.g. Charles A. Hasemann and J. Donald Capra, Immunoglobulins: Structure and Function, in William E. Paul, ed., Fundamental Immunology, Second Edition, 209, 210–218 (1989).

Crystal: A crystal is an array of molecules that occupy regular positions with respect to one another and form a solid of regular shape. Crystals form a precipitate when present in a solution because they are a solid.

Epitope: As used with reference to what a binding domain of a polypeptide purification reagent binds to, an epitope is the particular site within a protein of interest to which a specific binding domain binds.

$F_C$ portion of an antibody: An $F_C$ portion of an antibody includes human or animal immunoglobulin domains $C_H2$ and $C_H3$ or immunoglobulin domains substantially similar to these. See e.g. Hasemann and Capra, supra, at 212–213 (1989).

Means for specifically and reversibly binding a protein of interest: For purposes of the invention, a means for specifically and reversibly binding a protein of interest comprises a binding domain as discussed herein.

Means for forming a precipitate: For purposes of the invention, a means for forming a precipitate comprises any amino acid sequence within a polypeptide purification reagent that enables the polypeptide purification reagent to form a precipitate. More specifically, such sequences include: (1) sequences conferring a propensity to form a precipitate under conditions where the vast majority of proteins cannot by, for example, self-binding, crystallization, polyethylene glycol (PEG) precipitation, or salting out; (2) sequences conferring the ability to form an aggregate comprising the polypeptide purification reagent and another molecule, virus, cell, or portion thereof to which the polypeptide purification reagent can bind; and (3) binding domains which, when bound to a protein of interest, enable the protein of interest and the polypeptide purification reagent to form a precipitable polymer as illustrated in FIGS. 4A and 4B. Thus, a binding domain may also serve as a means for forming a precipitate.

Means for separating a protein of interest from a polypeptide purification reagent: A means for separating a protein of interest from a polypeptide purification reagent includes any amino acid sequence that allows this separation to be made by: affinity chromatography; selective precipitation of the polypeptide purification reagent without the protein of interest bound to it; or a separation based on differences in size, charge, and/or hydrophobicity between the protein of interest and the polypeptide purification reagent. Such sequences include, among others, protein tags, sequences conferring a propensity to form a precipitate, sequences conferring the ability to form an aggregate with another molecule, and sequences having an effect on the size, charge, or hydrophobicity of the polypeptide purification reagent.

Multimer: A multimer is a group of two or more proteins in close physical proximity to each other, which are held together by covalent bonds, hydrophobic interactions, hydrogen bonds, van der Waals forces, or other weak or strong interactions.

Non-antibody polypeptide: A non-antibody polypeptide is one that does not comprise an immunoglobulin or immunoglobulin-like domain. Known immunoglobulin domains are described in Kabat Sequences of Proteins of Immunological Interest (1987 and 1991, National Institutes of Health, Bethesda, Md.), or Chothia & Lesk, 1987, *J. Mol. Biol.* 196:901–917. Immunoglobulin-like domains are described in, e.g., Bork et al. (1994), *J. Mol. Biol.* 242: 309–20. Hunkapiller and Hood (1989), *Adv. Immunol.* 44:1–63; Miller et al. (1991), *Proc. Natl. Acad. Sci. USA* 88:4377–81; Williams and Barclay (1988), *Ann. Rev. Immunol.* 6:381–405.

Polypeptide purification reagent: A polypeptide purification reagent is a molecule, which comprises protein, that can reversibly and specifically bind to a protein of interest and can be used to purify the protein of interest by the methods of the invention. A polypeptide purification reagent comprises a binding domain and a scaffold domain, which are both polypeptides and which may or may not be distinct polypeptides. Thus, although a polypeptide purification reagent may comprise molecular structures other than polypeptides, the portions of a polypeptide purification reagent that bind to the protein of interest and that confer upon the polypeptide purification reagent a propensity to precipitate or to partition into a specific liquid phase in a liquid—liquid phase system are polypeptides.

Precipitate: A precipitate is a solid that separates out from a solution or suspension. For the purposes of the invention, the formation of a precipitate does not have substantial effects on the functional properties of the precipitated proteins.

Precipitable polymer: As meant herein, a precipitable polymer is a substance made up of one or more branched or unbranched chains of noncovalently and reversibly associated repeated units that forms a precipitate when the units are associated, but not when the units are dissociated. Examples of precipitable polymers are shown in FIGS. 4A and 4B. The precipitate formed by a precipitable polymer lacks the regular shape of a crystalline precipitate.

Protein A: Protein A is a protein originally discovered in the cell wall of *Stapphylococcus* that binds specifically and reversibly to an $F_C$ portion of IgG antibody. For purposes of the invention, "Protein A" is any protein identical or substantially similar to Stapphylococcal Protein A, including commercially available and/or recombinant forms of Protein A.

Protein G: Protein G is a protein originally discovered in the cell wall of *Streptococcus* that binds specifically to an $F_C$ portion of an IgG antibody. For purposes of the invention, "Protein G" is any protein identical or substantially similar to Streptococcal Protein G, including commercially available and/or recombinant forms of Protein G.

Protein L: Protein L is a protein originally isolated from the cell wall of *Peptostreptococcus*, which binds to antibody light chains and IgG, IgA, and IgM. See Akerstrom and Bjorck (1989), *J. Biol. Chem.* 264(33):19740–19746. For purposes of the invention, "Protein L" is any protein identical or substantially similar to Protein L, including commercially available and/or recombinant forms of Protein L.

Protein tag: A protein tag is an amino acid sequence of less than 35 amino acids that can specifically and reversibly bind to an affinity reagent and can be fused to another protein to form a recombinant fusion protein, which can be purified by virtue of the capacity of the protein tag to bind to the affinity reagent.

Purify: For the purposes of the invention, a composition comprising a protein is "purified" when the degree of purity of the protein is increased by removing (completely or partially) one or more contaminants.

Recombinant fusion protein: A recombinant fusion protein is a fusion of all or part of at least two proteins made using recombinant DNA technology.

Recombinant protein: A recombinant protein is a protein made using recombinant DNA technology.

Reversible binding: Reversible binding occurs when a molecule can bind to and dissociate from another molecule under conditions that will not prevent the repetition of this cycle by the same molecules.

Scaffold domain: For the purposes of the invention, a scaffold domain is a polypeptide that is capable of displaying one or more binding domains in a way such that the binding domains can specifically and reversibly bind to a protein of interest.

Self-binding domain: For the purposes of the invention, a self-binding domain is a polypeptide domain that, optionally, may be part of a scaffold domain, which is part of a polypeptide purification reagent. A self-binding domain can bind to the polypeptide purification reagent, of which it is a part. However, a self-binding domain cannot bind to the molecule of the polypeptide purification reagent on which it is situated; it can bind to a different molecule of the polypeptide purification reagent. A self-binding domain can bind either to an identical self-binding domain or to a different portion of the polypeptide purification reagent.

Specific binding: Specific binding by a protein occurs when the protein can bind to another molecule under conditions in which it does not bind to most other molecules. Evidence of specific binding of a molecule to a protein may be the fact that the bound molecule can be dislodged only by an excess of another molecule that binds specifically to the same or an overlapping binding site on the protein and not by an excess of any other molecule.

Substantially purified: A "substantially purified" protein is a preparation of a protein in which the protein comprises at least about 80%, preferably at least about 90%, more preferably at least about 95% of the protein present in the preparation.

Substantially similar: For purposes of the invention, proteins are substantially similar if they are at least 80%, preferably at least 90% identical to each other in amino acid sequence over at stretch of at least 10, optionally at least 20, 30, 40, 60, 80, 100, 150, or 200, amino acids and maintain or alter in a desirable manner the biological activity of the unaltered protein. Included in amino acids considered identical for the purpose of determining whether proteins are substantially similar are amino acids that are conservative substitutions, unlikely to affect biological activity, including the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and these changes in the reverse. See e.g. Neurath et al., *The Proteins*, Academic Press, New York (1979). The percent identity of two amino acid sequences can be determined by comparing sequence information using the Genetics Computer Group (GCG; Madison, Wis.) Wisconsin package version 10.0 program, GAP (Devereux et al. (1984), *Nucleic Acids Res.* 12:387–95). The preferred default parameters for the GAP program includes: (1) the weighted amino acid comparison matrix of Gribskov and Burgess, ((1986) *Nucleic Acids Res.* 14:6745) as described in *Atlas of Polypeptide Sequence and Structure*, Schwartz and Dayhoff, eds., National Biomedical Research Foundation, pp. 353–358 (1979) or other comparable comparison matrices; (2) a penalty of 8 for each gap and an additional penalty of 2 for each symbol in each gap; (3) no penalty for end gaps; and (4) no maximum penalty for long gaps.

TNFR: "TNFR" refers to proteins comprising amino acid sequences that are identical or substantially similar to the sequence of a native mammalian tumor necrosis factor receptor (TNFR). Biological activity for the purpose of determining substantial similarity means the capacity to bind tumor necrosis factor (TNF), to transduce a biological signal initiated by TNF binding to a cell, and/or to cross-react with anti-TNFR antibodies raised against TNFR from natural (i.e., non-recombinant) sources. A TNFR may be any mammalian TNFR, including murine or human TNFRs. Such TNFRs are described in U.S. Pat. No. 5,395,760 and in U.S. Pat. No. 5,610,279. A preferred TNFR is that described in U.S. Pat. No. 5,395,760, which has an apparent molecular weight by SDS-PAGE of about 80 kilodaltons in its glycosylated form.

TNFR: $F_C$: TNFR: $F_C$ is a recombinant fusion protein comprising all or part of an extracellular domain of any of the above-described TNFRs (including the p55 and p75 TNFRs) fused to an $F_C$ region of an antibody. Such an extracellular domain includes, but is not limited to, amino acid sequences substantially similar to amino acids 1–163, 1–185, and/or 1–235 of FIG. 2A of U.S. Pat. No. 5,395,760.

Variable antibody immunoglobulin domain: A variable antibody immunoglobulin domain is an immunoglobulin domain that is identical or substantially similar to a $V_L$ or a $V_H$ domain of human or animal origin.

DESCRIPTION

The invention encompasses polypeptide purification reagents and methods for making and using polypeptide purification reagents to purify virtually any protein of interest. A polypeptide purification reagent can specifically bind to a protein of interest and enable its purification by selective precipitation or by liquid—liquid extraction. Compositions of matter comprising such polypeptide purification reagents are encompassed by the invention. Methods of the invention enable repeated purification cycles without resort to column chromatography. Such methods enable a high throughput purification of a protein of interest in a relatively small volume, which is likely to be less expensive than relatively high-volume methods such as column chromatography.

In one aspect, the methods of the invention encompass using polypeptide purification reagents to bind to the protein of interest, enabling recovery of both the protein of interest and the reagent as a precipitate. In another aspect, the methods of the invention encompass using polypeptide purification reagents to bind to the protein of interest, enabling the extraction of both in a liquid—liquid extraction. For a discussion of liquid—liquid extraction techniques, see e.g. Scopes, Protein Purification: Principles and Practice, Third Edition, pp. 264–67. In either of these embodiments, the functional properties of both the protein of interest and the polypeptide purification reagent are essentially unaffected and the levels of contaminants present as compared to the starting mixture are reduced. The methods of the invention further encompass separating the polypeptide purification reagent from the protein of interest to obtain the polypeptide purification reagent, which can be reused, and a purified form of the protein of interest.

The polypeptide purification reagents encompassed by the invention can be, themselves, proteins and comprise at least one scaffold domain and at least one binding domain. Scaffold domains and binding domains are not necessarily distinct. A single domain may, but need not, serve both functions. Polypeptide purification reagents can be monomers or a multimers. The scaffold domain(s) can display the binding domain(s) in such a way that the binding domain(s) can bind to a protein of interest. Some embodiments of the polypeptide purification reagent have at least two binding domains and at least one scaffold domain. A polypeptide purification reagent comprising multiple binding domains can bind to multiple epitopes. These epitopes may be identical to or different from each other. If a polypeptide purification reagent can bind to at least two epitopes on a protein of interest, then, optionally, binding of plural molecules of a protein of interest by plural molecules of the polypeptide purification reagent results in the formation of a precipitable polymer that can form a precipitate comprising the polypeptide purification reagent and the protein of interest. A polypeptide purification reagent may or may not comprise a protein tag and/or a peptide linker. A polypeptide purification may or may not comprise a domain that confers a propensity to form a precipitate, a domain that facilitates purification by liquid—liquid extraction, or a domain that facilitates the formation of an aggregate in the presence of a cell, virus, molecule, or portion thereof. In an alternative embodiment, all or part of the polypeptide purification reagent can be non-peptide, such as, for example, an RNA or DNA moiety. The terms "protein" and "polypeptide" are used interchangeably herein.

Binding Domains

A binding domain is a polypeptide, which can include all or part of a polypeptide known to specifically and reversibly bind to a protein of interest or a substantially similar protein. Examples include all or part of Protein A, Protein G, and Protein L, which bind to antibodies, and all or part of antibodies and receptors that bind to any of the proteins of interest described below. See Miller and Stone (1978), J. Immunol. Methods 24(1–2): 111–25; Aybay and Imir (2000), J. Immunol. Methods 233(1–2):77–81; Vola et al. (1994), Cell Biophys. 24–25:27–36. One of skill in the art, will be aware of the conditions necessary for the binding of known proteins to known ligands.

Alternatively, a binding domain can be a polypeptide selected in vitro. Such selections may occur entirely in vitro. For example, each individual polypeptide in a library of potential binding domains can be attached to nucleic acids encoding it, and those that bind to the protein of interest under chosen conditions can be selected. Since the polypeptides are attached to nucleic acids encoding them, subsequent operations, such as amplifying, cloning, or sequencing nucleic acids encoding effective binding domains are facilitated. Various schemes for such selections are known in the art, including antibody-ribosome-mRNA particles, ribosome display, covalent RNA-peptide fusions, or covalent DNA-RNA-peptide fusions. He and Taussig (1997), Nucleic Acids. Res. 25(24): 5132–5134; Hanes and Pluckthun (1997), Proc. Natl. Acad. Sci. 94:4937–4942; Roberts and Szostak (1997), Proc. Natl. Acad. Sci. 94:12297–12302; Lohse and Wright (2001), Curr. Opin. Drug Discov. Devel. 4(2):198–204; Kurz et al. (2000), Nucleic Acids Res. 28(18):E83; Liu et al. (2000), Methods Enzymol. 318: 268–93; Nemoto et al. (1997), FEBS Lett. 414(2):405–08; U.S. Pat. No. 6,261,804; WO0032823; and WO0034784. Alternatively, the binding domain may be selected in vitro using phage display or display on the surface of bacteria. See e.g. Parmley and Smith (1989), Adv. Exp. Med. Biol. 251:215–218; Luzzago et al. (1995), Biotechnol. Annu. Rev. 1:149–83; Lu et al. (1995), Biotechnology (NY) 13(4): 366–372. In these methods, each member of a library of binding domains can be displayed on individual phage particles or bacterial cells, and bacteria or phage that bind to a protein of interest under chosen conditions can be selected. Nucleic acids encoding the selected binding domains can be obtained by growing the selected phage or bacteria and isolating nucleic acids from them. In vitro selection methods may be employed repeatedly to obtain effective binding domains.

Such selected binding domains can be selected to bind and dissociate under desired sets of conditions. Such conditions may include: 1) binding in the presence but not the absence of calcium, magnesium, manganese, or other salts or metal ions or vice versa; 2) dissociating at a higher salt concentration than that in which binding occurs or vice versa, wherein salts include sodium chloride, sodium fluoride, sodium bromide, sodium acetate, sodium phosphate, sodium citrate, potassium chloride, potassium fluoride, potassium bromide, potassium acetate, potassium phosphate, potassium citrate, ammonium chloride, ammonium fluoride, ammonium bromide, ammonium acetate, ammonium phosphate, ammonium citrate, ammonium sulfate, and those of the Hofmeister series, among others (see Haschemeyer and Haschemeyer, Proteins: A Guide to Study by Physical and Chemical Methods, 368–71, John Wiley & Sons (1973); Scopes, Protein Purification: Principles and Practice, 80, Springer (1994)); 3) dissociating at a different pH than that at which binding occurs, wherein both binding and dissociation occur within the range between about pH 2.5 and about pH 11.5, preferably between about pH 5.5 and pH 8.5; and/or 4) binding at a different temperature than that at which dissociation occurs wherein both binding and dissociation occur within the range of about 0° C. and 40° C.

Scaffold Domains

A scaffold domain is a polypeptide that can display the binding domain(s) in a way such that they can bind to the protein of interest. Scaffold domains and binding domains need not be from different proteins and need not be distinct. That is, a single domain may serve as both a binding domain and a scaffold domain if it has the required characteristics. Scaffold domains can be monomeric or multimeric. If the polypeptide purification reagent comprises a protein tag, the scaffold domain can display it in such a way that it can bind to an affinity purification reagent. Optionally, a scaffold domain may comprise a self-binding domain, which binds either to itself or to another portion of the polypeptide purification reagent. A scaffold domain may confer on the polypeptide purification reagent a propensity to form a precipitate under conditions where the majority of proteins will not form a precipitate. In addition or as a further alternative, a scaffold domain may confer on the polypeptide purification reagent a propensity to partition into a specific liquid phase in a liquid—liquid phase system, which facilitates purification. A scaffold domain may have a defined three-dimensional structure. If a scaffold domain is multimeric, units of the multimer may be linked by peptide linkers. An example of a scaffold domain is a protein including a fibronectin type III domain, such as the protein frameworks described in WO0034784. Alternatively, the scaffold domain may comprise a multimer of these scaffold domains in which the units of the multimer are linked by peptide linkers.

Optionally, a scaffold domain may confer a propensity to precipitate under conditions where the vast majority of other proteins do not precipitate by one or more of the following mechanisms: forming crystals; "salting out;" precipitating upon a change of pH; precipitating upon a change of temperature; forming a precipitable polymer by binding to itself via a self-binding domain; and precipitating upon the addition of polymeric molecules such as polyethylene glycol (PEG). For explanations and examples of these processes see e.g. Englard and Seifter (1990), Methods in Enzmol. 182:285–300; Ingham (1990), Methods in Enzmol. 182: 301–306; Scopes, supra, pp. 71–101. Optionally, the conditions under which the scaffold domain has a propensity to precipitate include conditions under which the protein of interest can bind to the polypeptide purification reagent and conditions in which it cannot. Some embodiments of the scaffold domain can include all or part a C-type lectin. Mason et al. (1998), Am. J. Physiol. 275 (1 Pt. 1):L1–L13; Hoppe and Reid (1994), Structure 2:1129–1133. Alternate embodiments of the scaffold domain can comprise a coiled coil domain and/or a collagen-like domain. See e.g. Ogihara et al. (1997), Protein Science 6:80–88; Harbury et al. (1993), Science 262:1401–1406; Lovejoy et al. (1993), Science 259:1288–1293. Collagen, for example, can be salted out to form a precipitate under relatively mild conditions, including 1.2 molar sodium chloride or 0.02 molar dibasic sodium phosphate. Rhodes and Miller (1978), Biochemistry 17(17): 3442–48; Miller and Rhodes (1982), Meth. Enzymol. 82:33–64. Moreover, coiled coils of certain designs may lead to easy formation of crystals. Ogihara et al. (1997), Protein Science 6:80–88. Furthermore, since binding domains can be selected in vitro (see above), a self-binding domain, which binds to a polypeptide purification reagent under specific conditions, can be selected in vitro and thereafter linked to the polypeptide purification reagent (as part of the scaffold domain) by means of genetic engineering to provide a means for forming a precipitate with or without the protein of interest bound to the polypeptide purification reagent.

In one embodiment, a polypeptide purification reagent may comprise two domains joined by a peptide linker, a first domain selected in vitro to bind to the protein of interest and a second domain selected in vitro to bind to the first domain or to itself. One can select such domains for virtually any binding capacity using, for example, the protein frameworks and methods described in WO0034784. Of course, other methods and/or framework domains can be used to select desired domains. If both the first and second domains use the protein frameworks of WO0034784 or substantially similar proteins, the second domain may be selected among those proteins that form precipitates under defined conditions. Thus, the first domain is acting as a binding domain, and the second is acting as a scaffold domain. Such a polypeptide purification reagent can have the property that the second domain (or scaffold domain) cannot bind to a domain that it is covalently linked to; that is, the second domain can bind only to first or second domains on other molecules. Optionally, such a second domain can bind to the first domain or to itself under conditions where the first can bind to the protein of interest and also under conditions where the first domain cannot bind to the protein of interest.

Precipitation of scaffold domains can be effected by adjusting the conditions in various ways. For example, conditions allowing precipitation may include: alteration of PEG concentrations to at least 3%; alteration of salt concentrations; addition or elimination elements such as calcium, magnesium, manganese, or any other metal or ion that is necessary for the binding of a binding domain and/or a self-binding domain; alteration of pH within a range of about 2.5 to about 11.5; and alteration of temperature. Suitable salts may include salts comprising sulfate, acetate, chloride, bromide, fluoride, phosphate, and those elucidated by the Hofmeister series, among others. See e.g. Haschemeyer and Haschemeyer, supra; and Scopes, supra.

Optionally, the scaffold domain may confer a propensity to precipitate through the formation of an aggregate upon the addition of a cell, virus, molecule, or portion thereof to which the scaffold domain can bind. Such scaffold domains can include, for example, all or part of a C-type lectin. The phenomenon of aggregate formation by C-type lectins is described in, for example, Hoppe and Reid (1994), Structure 2:1129–1133. Conditions allowing precipitation of such scaffold domains can include adding a molecule, virus, cell, or portion thereof to which the scaffold domain can bind, wherein the binding causes aggregate formation. Such molecules, viruses, or cells, include glucan, influenza virus, *Escherichia coli*, *Cryptococcus neoformans, Aspergillus fumigatus*, and *Saccharomyces cerevisiae*, among others. See e.g. Brown-Augsburger et al. (1996), J. Biol. Chem. 271(31):18912–18919; Allen et al. (2001), Infection and Immunity 69(4):2037–2044; Lawson and Reid (2000), Immunological Reviews 173:66–78. Conditions allowing aggregate formation can include the addition of salts including those comprising calcium, magnesium, potassium, sodium, and/or ammonium, among others.

In another aspect, a scaffold domain may confer on a polypeptide purification reagent a propensity to partition into an aqueous liquid phase that is distinct from a second liquid phase into which at least some of the contaminants of the protein of interest partition. Such a liquid—liquid partitioning system comprises at least two immiscible liquid phases, each of which can dissolve proteins. See e.g. Scopes, supra, pp. 264–67. At least one of the phases has the capacity not to inactivate proteins. One such system comprises one aqueous phase that is dextran-rich and another that is PEG-rich. Other such systems are also available. See e.g. van Berlo et al (1999), J. Chromatogr. B Biomed. Sci. Appl. 711(1–2):61–68; de Belval et al. (1998), J. Chromatogr. B Biomed. Sci. Appl. 711(1–2):19–29; Truust and Johansson (1998), J. Chromatogr. B Biomed. Sci Appl. 711:117–26. In a PEG/dextran system, it is possible to attach affinity ligands to the ends of PEG molecules. A scaffold domain of a polypeptide purification reagent can comprise an amino acid sequence that binds to such a ligand, thus allowing it to partition into the PEG-rich phase, along with a protein of interest if it is bound to the polypeptide purification reagent. See Kopperschlager et al. (1983), J. Chromatogr. 259: 97–105. Since most proteins partition into the dextran-rich phase, partitioning into the PEG-rich phase can allow elimination of some protein contaminants.

Protein Tags

A polypeptide purification reagent may comprise a protein tag. Examples of protein tags include polyarginine, polyhistidine, or HAT™ (Clontech), which is a naturally-occurring sequence of non-adjacent histidine residues that possess a high affinity for immobilized metal ions. Suitable affinity reagents for poly-His or HAT™ protein tags include immobilized nickel or TALON™ resin (Clontech), which comprises immobilized cobalt ions. See e.g. Knol et al. (1996), J. Biol. Chem. 27(26): 15358–15366. Polyarginine tags allow effective purification by ion exchange chromatography. Other protein tags include, for example, the antigenic identification peptides described in U.S. Pat. No. 5,011,912 and in Hopp et al. (1988), Bio/Technology 6:1204. One such peptide is the FLAG® peptide, which is highly antigenic and provides an epitope reversibly bound by a specific monoclonal antibody, enabling rapid assay and facile purification of expressed recombinant fusion protein. A murine hybridoma designated 4E11 produces a monoclonal antibody that binds the FLAG® peptide in the presence of certain divalent metal cations, as described in U.S. Pat. No. 5,011,912. The 4E11 hybridoma cell line has been deposited with the American Type Culture Collection under accession no. HB 9259. Monoclonal antibodies that bind the FLAG® peptide can be used as affinity reagents to recover a polypeptide purification reagent that comprises the FLAG® peptide. Other suitable protein tags and affinity reagents are: 1) those described in GST-Bind™ system (Novagen), which utilizes the affinity of glutathione-S-transferase fusion proteins for immobilized glutathione; 2) those described in the T7-Tag® affinity purification kit (Novagen), which utilizes the affinity of the amino terminal 11 amino acids of the T7 gene 10 protein for a monoclonal antibody; or 3) those described in the Strep-tag® system (Novagen), which utilizes the affinity of an engineered form of streptavidin for a protein tag. Some of the above-mentioned protein tags, as well as others, are described in Sassenfeld (1990), TIBTECH 8:88–93, Brewer et al., in Purification and Analysis of Recombinant Proteins, pp. 239–266, Seetharam and Sharma (eds.), Marcel Dekker, Inc. (1991), and Brewer and Sassenfeld, in Protein Purification Applications, pp. 91–111, Harris and Angal (eds.), Press, Inc., Oxford England (1990).

Peptide Linkers

The domains in a polypeptide purification reagent can be advantageously linked using a peptide linker. Generally, a peptide linker is a stretch of amino acids that serves to link plural identical, similar, or different polypeptides to form multimers and provides the flexibility or rigidity required for the desired function of the linked portions of the protein. Typically, a peptide linker is between about 1 and 30 amino acids in length. Examples of peptide linkers include, but are not limited to, --Gly-Gly--, GGGGS (SEQ ID NO:1), (GGGGS)n (SEQ ID NO:2), GKSSGSGSESKS (SEQ ID NO:3), GSTSGSGKSSEGKG (SEQ ID NO:4), GSTSGS-GKSSEGSGSTKG (SEQ ID NO:5), GSTSGSGKSSEGKG (SEQ ID NO:6), GSTSGSGKPGSGEGSTKG (SEQ ID NO:7), or EGKSSGSGSESKEF (SEQ ID NO:8). Linking moieties are described, for example, in Huston, J. S., et al., PNAS 85:5879–5883 (1988), Whitlow, M., et al., Protein Engineering 6:989–995 (1993), and Newton, D. L., et al., Biochemistry 35:545–553 (1996). Other suitable peptide linkers are those described in U.S. Pat. Nos. 4,751,180 and 4,935,233.

Non-Peptide Linkers

The domains of a polypeptide purification reagent can also be linked, optionally covalently linked, using a non-peptide linker of almost any molecular nature. However, such a linker serves the function of linking the domains of a polypeptide purification reagent and cannot, by itself, be induced to precipitate by adjusting conditions. For example, the term "non-peptide linkers," as meant herein, specifically excludes molecules such as alginic acid or the "smart" polymers that can be induced to precipitate by various changes of conditions. See e.g. Coughlin et al. (1976), Biotechnol. Bioeng. 18:199–208; Galaev and Mattiasson (1999), TIBTECH 17:335–40; Hoffman et al. (2000), J. Biomed. Mater. Res. 52:577–86. Suitable non-peptide linkers include, for example, molecules such as those discussed in connection with linking two NAD or two ATP molecules by Irwin and Tipton ((1996), Methods in Molecular Biology 59:217–38) and Larsson and Mosbach ((1979), FEBS Letters 98(2):333–38). The length of a non-peptide linker can be adjusted to allow, for example, two binding domains each to bind to a protein of interest. By linking, for example, plural binding domains, a non-peptide linker may confer upon a polypeptide purification reagent as a whole the ability to form a precipitable polymer when bound to a protein of interest, particularly a multimeric protein of interest.

Proteins of Interest

A protein of interest can be any protein of commercial, economic, pharmacologic, diagnostic, or therapeutic value. Proteins of interest contemplated by the invention include monomeric and multimeric proteins. Proteins of interest include, but are not limited to, polypeptides comprising proteins identical or substantially similar to one of the following proteins: a flt3 ligand, a CD40 ligand, erythropoeitin, thrombopoeitin, calcitonin, Fas ligand, ligand for receptor activator of NF-kappa B (RANKL), tumor necrosis factor (TNF)-related apoptosis-inducing ligand (TRAIL), thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor, leukemia inhibitory factor, oncostatin-M, and various ligands for cell surface molecules ELK and Hek (such as the ligands for eph-related kinases or LERKS). Descriptions of proteins that can be expressed according to the inventive methods can be found in, for example, *Human Cytokines: Handbook for Basic and Clinical Research, Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991). Proteins of interest also encompass antibodies that bind to the above-mentioned proteins.

Proteins of interest contemplated by the invention also include polypeptides comprising a receptor for any of the above-mentioned proteins or proteins substantially similar to such receptors. These receptors include: both forms of tumor necrosis factor receptor (TNFR, referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR). Proteins of interest also encompass antibodies that bind to the above-mentioned receptors.

Proteins of interest also include differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD27, CD30, CD39, CD40, and ligands thereto (CD27 ligand, CD30 ligand, etc.). Several of the CD antigens are members of the TNF receptor family, which also includes 41BB ligand and OX40. The ligands are often members of the TNF family, as are 41BB ligand and OX40 ligand. Accordingly, proteins of interest comprising TNF, TNFR, TNFR:Fc or proteins substantially similar to these can also be purified using the present invention. Proteins of interest also encompass antibodies that bind to the above-mentioned differentiation antigens or their ligands.

Enzymatically active proteins or their ligands can also be proteins of interest and can be purified according to the invention. Examples include polypeptides comprising all or part of one of the following proteins or their ligands or a protein substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands. Proteins of interest also encompass antibodies that bind to the above-mentioned enzymatically active proteins or their ligands.

The method of the invention can also be used to purify proteins of interest comprising any and all antibodies or portions thereof and chimeric antibodies, e.g. antibodies having human constant antibody immunoglobulin domains coupled to one or more murine variable antibody immunoglobulin domain, or fragments thereof. The method of the invention can also be used to purify conjugates comprising an antibody and a cytotoxic or luminescent substance. Such substances include: maytansine derivatives (such as DM1); enterotoxins (such as a Staphlyococcal enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6). Examples of proteins of interest comprising antibodies or antibody/cytotoxin or antibody/luminophore conjugates contemplated by the invention include those that recognize the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-4, IL-5, IL-8, IL-10, IL-2 receptor, IL-6 receptor, PDGF-β, VEGF, TGF, TGF-β2, TGF-β1, EGF receptor, VEGF receptor, C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA4, B2 integrins, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human immunodeficiency virus (HIV), hepatitis B virus (HBV), *Streptococcus mutans*, and *Staphlycoccus aureus*.

The invention can also be used to purify anti-idiotypic antibodies or substantially similar proteins, including anti-idiotypic antibodies against: an antibody targeted to the tumor antigen gp72; an antibody targeted to the ganglioside GD3; or an antibody targeted to the ganglioside GD2.

Methods of Making Proteins of Interest and Polypeptide Purification Reagents

Any of the proteins of interest or polypeptide purification reagents described herein can be obtained by recombinant techniques. For example, one can (1) insert nucleotide sequences encoding either polypeptide into a recombinant vector designed to allow expression and, optionally, secretion of inserted sequences, (2) introduce the recombinant vector with the inserted nucleotide sequences into living cells that can express the inserted nucleotide sequences, (3) culture the cells under conditions in which the inserted sequences are expressed, and (4) recover the protein of interest or polypeptide purification reagent from the cultured cells. Various methods of performing recombinant expression techniques are well known in the art. See e.g. Sambrook et al., Molecular Cloning: A Laboratory Manual, Second Edition, Vol. 1–3, Cold Spring Harbor Press (1989); Pouwels et al., *Cloning Vectors: A Laboratory Manual*, Elsevier, New York (1985); Kaufman, *Large Scale Mammalian Cell Culture*, (1990); Felgner et al. (1987), Proc. Natl. Acad. Sci. USA 84:7413–7417; Hinnen et al. (1978), Proc. Natl. Acad. Sci. USA 75:1929; Kaufman et al. (1990), Methods Enzymol. 185:487–511. Suitable host cells include bacterial, fungal, animal, or human cells. Examples of such cells include *Escherichia coli* cells, *Bacillus subtilis* cells, *Salmonella typhimurium* cells, cells from various species within the genera *Pseudomonas*, *Streptomyces*, and *Staphylococcus*, *Saccharomyces cerevisiae* cells, *Pichia pastoris* cells, cells from fungii of other genera such as *Klyveromyces* or *Aspergillus*, and CHO, VERO, BHK, HeLa, Cos, MDCK, 293, 3T3, and WI38 cells, among others. Optionally, the protein can be secreted by the cells into the media. Such a secreted protein can be recovered by harvesting the medium in which the cells have been grown. Medium can be harvested by separating the cells from the medium by any appropriate means, including, for example, centrifugation.

The polypeptide purification reagent can be purified using standard techniques. In addition, if the polypeptide purification reagent has a propensity to precipitate or to partition away from most proteins in a liquid—liquid phase system, these properties can be used to purify it. The protein of interest can be subjected to an initial partial purification using known techniques, such as chromatography, among other techniques.

Illustrations of Polypeptide Purification Reagents and Proteins of Interest

For the purposes of illustration and not limitation, various possible embodiments of the polypeptide purification reagent are shown in the accompanying figures. FIG. 1A shows a polypeptide purification reagent 1 that comprises one binding domain 3 that binds to an epitope on the protein of interest and one scaffold domain 5. The scaffold domain 5 includes amino acid sequences that confer a propensity to precipitate (as explained above), which is indicated by horizontal lines across the scaffold domain 5.

FIG. 1B depicts a polypeptide purification reagent 11 comprising two binding domains 3 and 15 and one scaffold domain 5. In this embodiment, each binding domain 3 and 15 can bind to a different epitope on a protein of interest, as indicated by their different patterns (checkerboard vs. diagonal lines). The scaffold domain 5, like that in FIG. 1A, has a propensity to form a precipitate.

FIG. 1C depicts another embodiment of a polypeptide purification reagent 21 comprising two binding domains 3 and 3 and one scaffold domain 5. The binding domains 3 and 3 can bind to identical epitopes on the protein of interest, as indicated by their identical patterns (checkerboard). The scaffold domain 5, like that in FIG. 1A, has a propensity to form a precipitate.

FIG. 1D depicts another embodiment of a polypeptide purification reagent 31 comprising two binding domains 3 and 3 and one scaffold domain 33. The binding domains 3 and 3 can bind to identical epitopes on the protein of interest, as indicated by their identical patterns (checkerboard). The scaffold domain 33, unlike that in FIG. 1A, does not have a propensity to form a precipitate.

FIG. 1E depicts another embodiment of a polypeptide purification reagent 41 comprising two binding domains 3 and 15 and one scaffold domain 33. In this embodiment, each binding domain 3 and 15 can bind to a different epitope on a protein of interest, as indicated by their different patterns (checkerboard vs. diagonal lines). The scaffold domain 33, unlike that in FIG. 1A, does not have a propensity to form a precipitate.

Embodiments of the polypeptide purification reagent comprising more than one binding domain (11, 21, 31, and 41 of FIGS. 1B–1E) may, optionally, have the following additional properties. When plural binding domains are situated on the same, single molecule of a polypeptide purification reagent 11, 21, 31, or 41, all of them cannot simultaneously bind to a single molecule of a protein of interest. That is, the binding of at least one of these plural binding domains to a molecule of the protein of interest can preclude the binding of at least one other binding domain to the same molecule of the protein of interest for steric reasons. However, two such binding domains can bind simultaneously if they bind to at least two different molecules of the protein of interest.

FIG. 1F diagrammatically depicts two embodiments of a protein of interest, a monomeric protein 51 and a dimeric protein 53.

Methods of the Invention

Formation of a Precipitate Comprising the Protein of Interest and the Polypeptide Purification Reagent A protein of interest and polypeptide purification reagent can be combined under conditions where the polypeptide purification reagent can bind to the protein of interest. The protein of interest and the polypeptide purification reagent can then form a precipitate. Adjustment of the conditions may or may not be necessary to cause precipitation. Precipitation may occur in any one of several ways.

First, the polypeptide purification reagent with the protein of interest bound to it may be induced to form crystals by an appropriate adjustment of the conditions. As stated above, it is advantageous if such conditions do not induce the vast majority of proteins to precipitate. As discussed above, such adjustments can include addition of polymeric molecules such as PEG at concentrations of at least 3%, addition of salt(s), and/or adjustment of pH or temperature, depending on the nature of the scaffold domain. A diagrammatic representation of such crystals, comprising polypeptide purification reagent 1 of FIG. 1A and a protein of interest, are shown in FIG. 2B. Other representations of such crystals, comprising polypeptide purification reagent 11 or 21 plus a protein of interest, are shown in FIGS. 3B and 3C, respectively.

Alternatively, the polypeptide purification reagent with the protein of interest bound to it may be induced to form a precipitate by salting it out or precipitating it with a polymeric molecule such as PEG, as described above.

As another alternative, conditions can be adjusted such that a self-binding domain forming part of a polypeptide purification reagent can bind, thus causing the formation of a precipitable polymer.

As a further alternative, the polypeptide purification reagent with the protein of interest bound to it can be induced to form a precipitate by adding a cell, virus, molecule, or portion thereof that the scaffold domain can bind to, thereby causing the formation of an aggregate. As an example, this alternative is appropriate for embodiments of a polypeptide purification reagent comprising a scaffold domain including all or part of a C-type lectin. One of skill in the art will recognize that if the scaffold comprises a C-type lectin or a substantially similar protein, calcium can be added to facilitate binding and aggregate formation. Other scaffold domains may require other adjustments to the conditions in order to form aggregates.

As still another alternative, binding of a protein of interest to a polypeptide purification reagent may cause precipitation due to the formation of a precipitable polymer. For example, the polypeptide purification reagents 11 or 41 (FIG. 1B or 1E) can form a precipitable polymer by binding to a protein of interest such as 51 (FIG. 1F), as illustrated for polypeptide purification reagent 11 in FIG. 4A. Alternatively, polypeptide purification reagents 21 or 31 (FIG. 1B or 1C), which have two identical binding domains, may also form such a precipitable polymer with multimeric proteins of interest such as 53 (FIG. 1F), as illustrated in FIG. 4B.

Separation of the Precipitate from the Solution

The precipitate can be separated from the solution by any appropriate means, including centrifugation and/or filtration. This separation can result in a purification of the protein of interest. The precipitate may be washed.

Repurification (Optional)

Optionally, the protein of interest may be repurified by one or more reprecipitations, optionally using a different method(s) than what was used in the previous precipitation step(s). For example, if the protein of interest and polypeptide purification reagent were previously precipitated by formation of crystals, a second precipitation by formation of precipitable polymers can be appropriate. Similarly, if a first precipitation involved formation of precipitable polymers, a second precipitation by formation of crystals, can be appropriate. This second precipitation can be done under conditions where the protein of interest remains bound to the polypeptide purification reagent in order to further purify the protein of interest. Alternatively, a second precipitate may be formed by formation of an aggregate, as described above. Appropriate adjustments of conditions to cause these second precipitations are discussed above in relation to the first precipitation.

As an example, the polypeptide purification reagent 1 of FIG. 1A with the protein of interest bound to it can be first precipitated by inducing crystal formation, as diagrammed in FIG. 2B. After separation of the precipitate from the solution and resuspension of the precipitate under conditions in which the protein of interest can bind to the polypeptide purification reagent, reprecipitation can be induced by adjusting conditions such that an aggregate forms and crystals do not form.

As an alternative example, the polypeptide purification reagent 11 of FIG. 1B with the protein of interest bound to it can be first precipitated by the formation of precipitable polymers, as illustrated in FIG. 4A. The precipitate can be separated from the solution and resuspended under conditions such that one, but not both, binding domains can bind to the protein of interest, thereby preventing formation of precipitable polymers. By appropriate adjustments to the conditions, crystal formation can be induced to precipitate the polypeptide purification reagent 11 bound to the protein of interest 51 a second time, as shown in FIG. 3B. Alternatively, polypeptide purification reagent 11 may comprise a self-binding domain, and conditions can be adjusted such that the polypeptide purification reagent can bind to itself, thus causing the formation of precipitable polymers. Other sequences of two successive precipitations are also possible.

As a further alternative, the protein of interest may be repurified by subjecting the protein of interest/polypeptide purification reagent complex to affinity chromatography. To do this, the polypeptide purification reagent should be able to bind the protein of interest without forming a precipitate and should, furthermore, be able to bind to an affinity reagent while bound to the protein of interest. Polypeptide purification reagents 1, 11, and 41 (FIGS. 1A, 1B, and 1E) can be appropriate reagents for repurification by affinity chromatography; and polypeptide purification reagent 21 and 31 (FIGS. 1C and 1D) may also be appropriate for monomeric proteins of interest. To effect purification, the polypeptide purification with the protein of interest bound to it is combined with an affinity reagent, and conditions can be adjusted so that the polypeptide purification reagent can bind to the affinity reagent while bound to the protein of interest. The protein of interest can be eluted by an appropriate adjustment of conditions, either by itself or bound to the protein of interest. Appropriate elution conditions will depend on the conditions for binding of the affinity reagent and the protein of interest by the polypeptide purification reagent.

Separation of the Precipitate from the Solution

If the repurification involves a second precipitation rather than affinity purification, the precipitate can be separated from the solution by any appropriate means, including centrifugation and/or filtration. This separation can result in a purification of the protein of interest. The precipitate may be washed.

Separation of the Protein of Interest from the Polypeptide Purification Reagent

The protein of interest can be separated, if necessary, from the polypeptide purification reagent by any appropriate means, including: affinity chromatography; reprecipitation of the polypeptide purification reagent without the protein of interest bound to it; or a separation based on differences in size, charge, or hydrophobicity between the protein of interest and the polypeptide purification reagent.

Figure 2A:
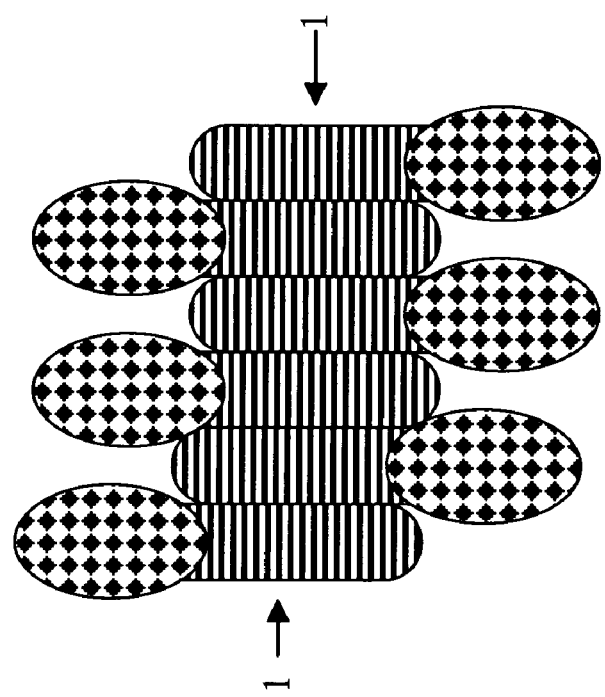
FIG. 2A represents the crystallization of polypeptide purification reagent 1 (FIG. 1A) when it is not bound to a protein of interest.

To separate the protein of interest from the polypeptide purification reagent by reprecipitation, these proteins can be subjected to conditions such that the polypeptide purification reagent cannot bind to the protein of interest. Optionally, the conditions will be similar, although not identical, to conditions in which at least one previous purification step involving precipitation has occurred. Thereafter, conditions can be adjusted such that the polypeptide reagent, but not the protein of interest, forms a precipitate by any of the mechanisms described above, including crystal formation, PEG precipitation, salting out, self-binding, or aggregate formation. Examples of such precipitates formed by crystallization are shown in FIGS. 2A and 3A for polypeptide purification reagents 1 and 11 of FIGS. 1A and 1B, respectively. The precipitate, comprising the polypeptide purification reagent, can be separated from the solution, comprising the protein of interest, by any appropriate means including filtration or centrifugation.

This method of separation of the protein of interest from the polypeptide purification reagent also serves as a further purification of the protein of interest for the following reasons. If the previous purification of the protein of interest involved precipitating it, the major contaminants of the protein of interest are likely to be other molecules that precipitate readily under the conditions used. In the separation step, the protein of interest is ultimately in solution rather than in the precipitate, and the conditions can be similar, although not identical, to the conditions used in the first precipitation. Therefore, most of the remaining contaminants are likely to precipitate. Thus, most contaminants of a protein of interest remaining after a purification by precipitation can be reduced or eliminated by a separation based on reprecipitation of the polypeptide purification reagent without the protein of interest bound to it.

To separate the protein of interest from the polypeptide purification reagent by affinity chromatography, the polypeptide purification reagent can comprise a protein tag. The protein of interest and the polypeptide purification reagent can be subjected to conditions such that the polypeptide purification reagent cannot bind to the protein of interest. Thereafter, affinity chromatography can be performed under conditions such that the polypeptide purification can bind to the affinity reagent, and the protein of interest cannot bind to either the affinity reagent or the polypeptide purification reagent. The protein of interest can be recovered in the flow through (material that does not bind to the affinity reagent). The polypeptide purification reagent can be eluted from the affinity reagent by an appropriate adjustment of conditions.

Separations based on differences in size, charge, or hydrophobicity are well known in the art and can be used in appropriate circumstances to separate protein of interest/polypeptide purification reagent pairs with differences large enough to make such separations possible.

An Alternative Purification Scheme for Polypeptide Purification Reagent Comprising a Domain that Facilitates Purification in a Liquid—Liquid Phase System As explained above, some polypeptide purification reagents may comprise amino acid sequences that facilitate purification in a liquid—liquid phase system. In this case, purification can comprise the following steps. Conditions can be adjusted such that the polypeptide purification reagent can bind to the protein of interest, as discussed above. If necessary, conditions can be readjusted such that at least two liquid phases form, for example, by adding appropriate concentrations of PEG and dextran. Thereafter, the phase that does not contain the polypeptide purification reagent and the protein of interest can be discarded, and the other phase may, but need not, be re-extracted. The polypeptide purification reagent and the protein of interest can be separated by adjusting conditions such that the polypeptide purification reagent cannot bind to the protein of interest and at least two phases can form, with the polypeptide purification reagent partitioning to a different phase than the protein of interest. In some embodiments, liquid—liquid extraction methods can be combined with the precipitation methods described above to purify a protein of interest.

Embodiments of the Invention Using a C-type Lectin-like Scaffold Domain

Illustrations of Polypeptide Purification Reagents Comprising a C-type Lectin

In one aspect of the methods of the invention, the scaffold domain of a polypeptide purification reagent comprises part or all of a trimeric C-type lectin 101. A C-type lectin is diagrammatically depicted in FIG. 5A. Such polypeptide purification reagents can comprise the neck region 103 of a C-type lectin and, optionally, the collagenous region 105, the carbohydrate recognition domain (CRD) 107, and/or the amino terminal domain 109 of a C-type lectin (FIG. 5A). Accordingly, this scaffold domain can form trimers (as do C-type lectins) and, optionally, higher order multimers, including multimers comprising four or six trimeric units. A dodecamer comprising four trimeric units is shown in FIG. 5B. See e.g. Mason et al., supra.

Several embodiments of the polypeptide purification reagent are illustrated in the figures, all of which associate to form trimers. A polypeptide purification reagent 111 (FIG. 6A) can include a scaffold domain 113 comprising an amino terminal domain 109, a neck region 103, and a collagenous region 105 of a C-type lectin. See e.g. Mason et al., supra; Hoppe and Reid, supra. Such scaffold domains 113 can be fused to binding domains 115, which are like the binding domains described above for FIGS. 1A–1E. Alternatively, a polypeptide purification reagent 117 (FIG. 6B) may include a scaffold domain 119 comprising an amino terminal domain 109, a neck region 103, a collagenous region 105, all or part of a CRD 107, and a binding domain 115 like those described above for FIGS. 1A–1E. Optionally, the CRD 107 may bind to its normal ligands in this embodiment (117).

In another set of embodiments diagrammed in FIGS. 7A–7C, a trimeric polypeptide purification reagent 111 or 117 can be formed under conditions that prevent formation of higher order multimers. Such conditions can include a reducing environment since higher order multimer formation requires the formation of disulfide bridges between trimers, which are mediated by cysteine residues in the amino terminal domains 109. Any appropriate reducing agent can be used. These include, but are not limited to, dithiothreitol, cysteine, and/or beta mercaptoethanol. This trimeric polypeptide purification reagent is combined with an unaltered trimeric C-type lectin formed under similar conditions. Conditions are then adjusted to allow formation of disulfide bonds so that higher order multimers, such as the dodecamers 120, 121, 122 shown in FIGS. 7A–7C can be formed. Such conditions can comprise an oxidizing environment, which can be created by any appropriate means. Such means include eliminating the reducing agent by dialysis or diafiltration and/or by addition of metals and/or air oxidation. Multimers 120, 121, 122 (FIGS. 7A–7C) comprising both a binding domain 115 that can bind to a protein of interest as well as a CRD 107 can be selected by any appropriate means including affinity chromatography. Alternatively, if the CRD of a polypeptide purification reagent 117 (FIG. 6B) is functional, a dodecamer comprising only polypeptide purification reagent 117, which can be formed under oxidizing conditions, is also an embodiment encompassed by the present invention.

In another embodiment shown in FIG. 8, a polypeptide purification reagent 123 can comprise a neck region 103, a CRD 107, a binding domain 115, and, optionally, a collagenous region 105. A binding domain 115 can be attached to any portion of the polypeptide purification reagent in which it can bind to the protein of interest without destabilizing its trimeric structure and without interfering with the binding properties of the CRD 107. Optionally, the binding domain may be attached by a flexible peptide linker 124 (FIG. 8).

The polypeptide purification reagent 125 (FIG. 9) is similar to the polypeptide purification reagent 123 (FIG. 8), except that a self-binding domain 127, which allows the polypeptide purification reagent to reversibly and specifically bind to itself under some conditions, replaces the CRD 107 of polypeptide purification reagent 123. Alternatively, the CRD may also be part of the polypeptide purification reagent. The self-binding domain 127 can bind to itself or another part of the polypeptide purification reagent under conditions where the polypeptide purification reagent can bind to the protein of interest and/or under conditions where the polypeptide purification reagent cannot bind to the protein of interest. Such a self-binding domain may comprise part or all of a known protein or a protein selected in vitro for the desired binding characteristics.

Figure 10B:
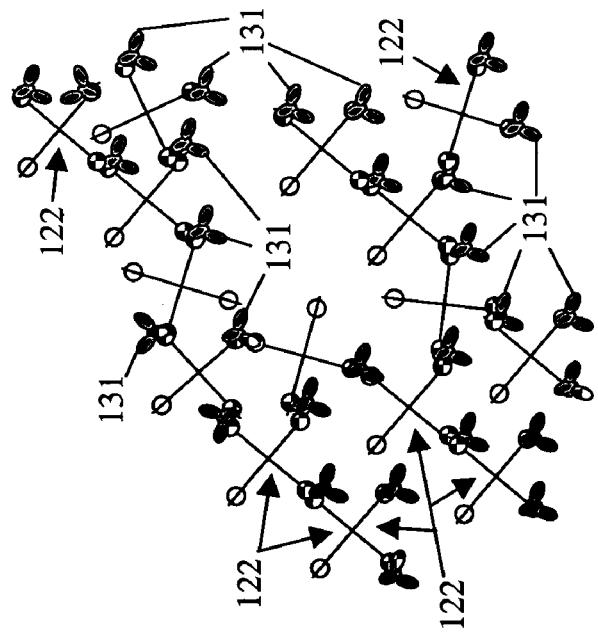
FIG. 10B depicts a precipitable polymer formed by binding of polypeptide purification reagent 122 (FIG. 7C) to a dimeric protein of interest.
Figure 10A:
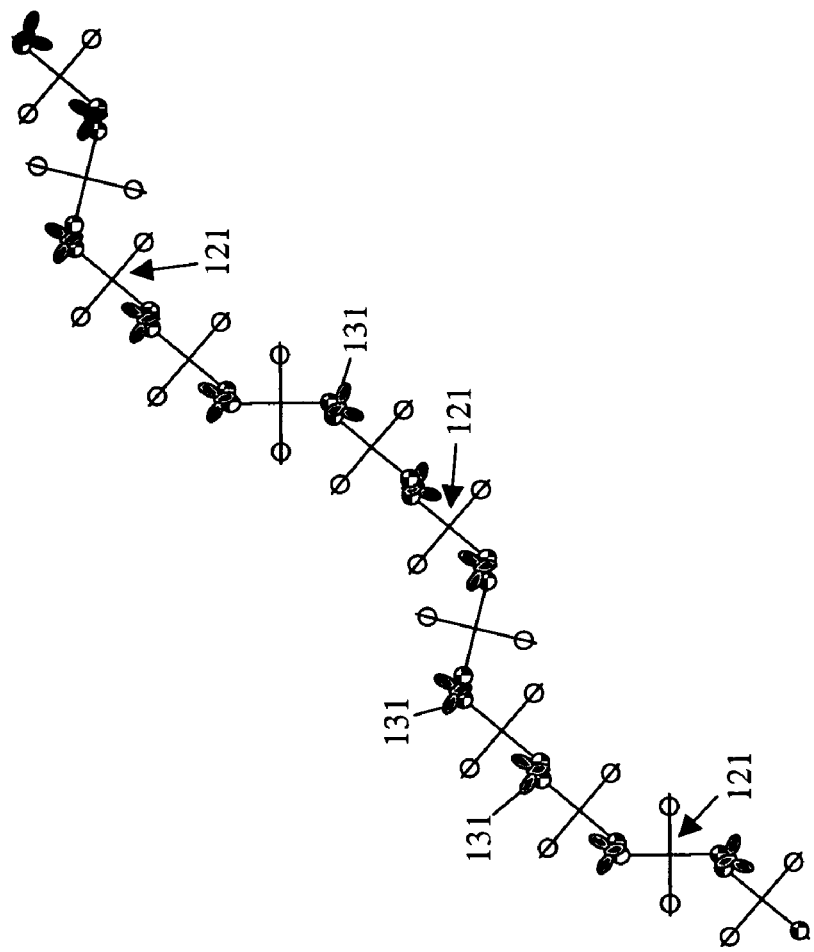
FIG. 10A depicts a precipitable polymer formed by binding of polypeptide purification reagent 121 (FIG. 7B) to a dimeric protein of interest.
Figure 11:
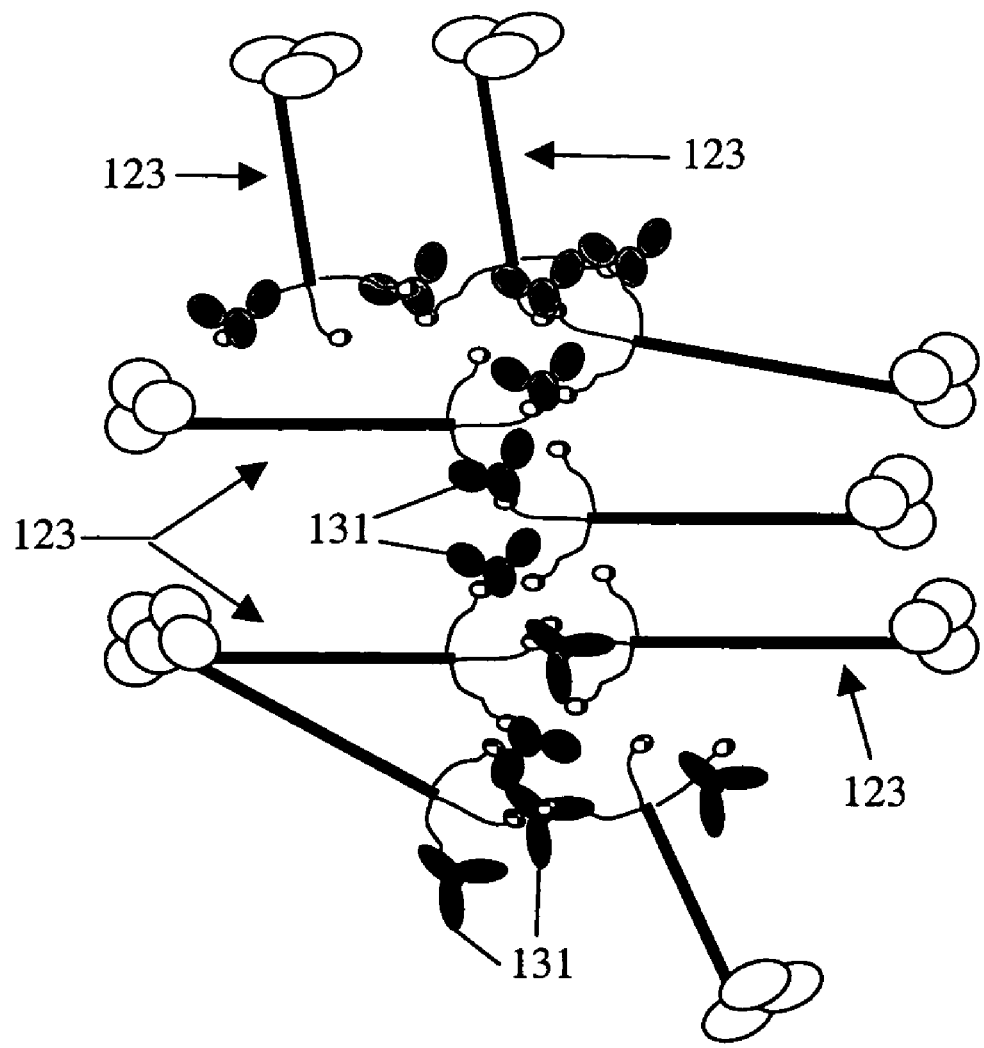
FIG. 11 depicts a precipitable polymer formed by binding of polypeptide purification reagent 123 (FIG. 8) to a dimeric protein of interest.

Methods of Using Polypeptide Purification Reagents Comprising All or Part of a C-type Lectin Polypeptide purification reagents 111, 117, 120, 121, 122, 123, and 125 (FIGS. 6A–9) can be used to purify a protein of interest, such as, for example, IgG, which is a dimeric molecule. In a first step, a polypeptide purification reagent 111, 117, 120, 121, 122, 123, 125 can be added to a solution comprising a dimeric protein of interest, such as IgG 131 (FIG. 10A), and conditions can be adjusted such that a binding domain 115 can bind to IgG 131. As shown, for example, in FIGS. 10A, 10B, 11, and 12A for polypeptide purification reagents 121, 122, 123, and 125, respectively, this can result in the formation of precipitable polymers. If necessary, conditions can be adjusted such that the precipitable polymers can form a precipitate.

Figures 12A, 12B:
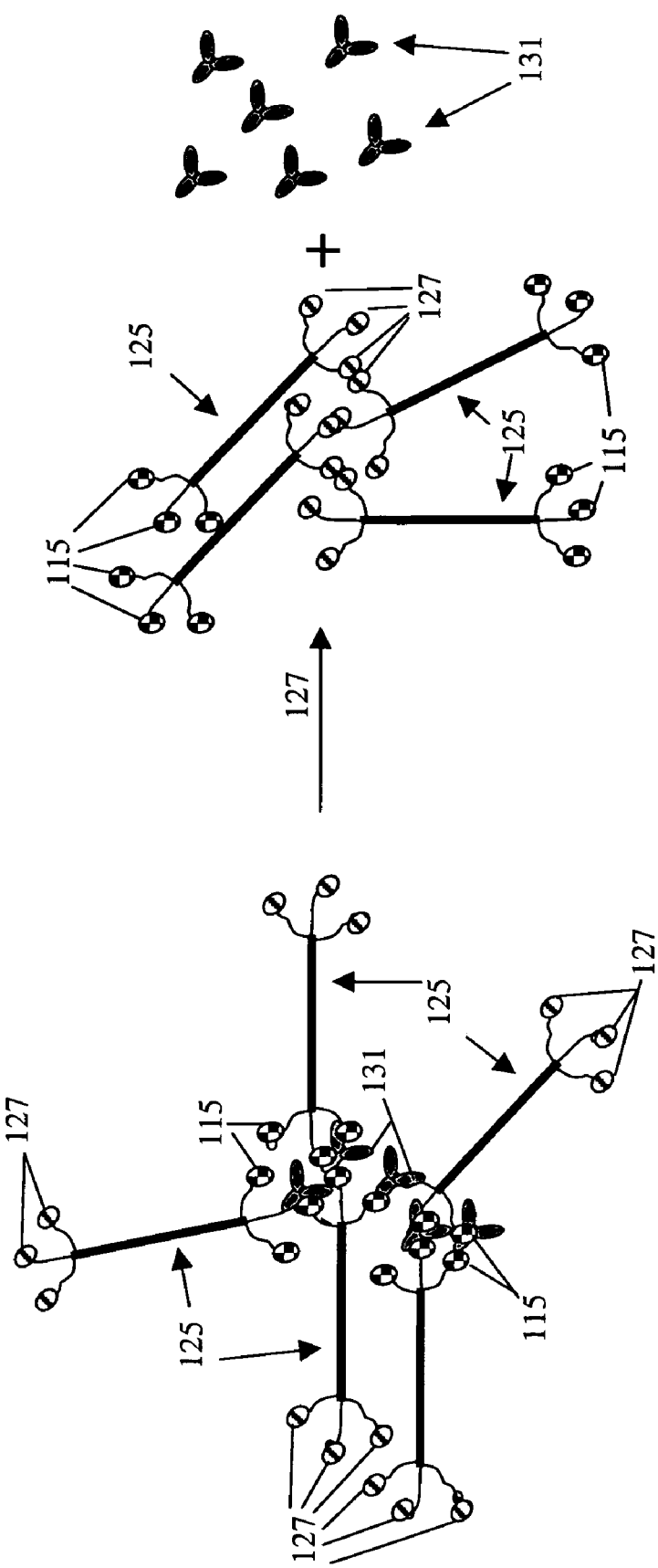
FIG. 12A depicts a precipitable polymer formed by binding of polypeptide purification reagent 125 (FIG. 9) to a dimeric protein of interest.
FIG. 12B depicts a precipitable polymer formed by binding of polypeptide purification reagent 125 (FIG. 9) to itself.

For polypeptide purification reagent 125 (FIG. 9), precipitable polymers may be formed by an alternate mechanism, that is, self-binding, which does not depend on the protein of interest being multimeric. Polypeptide purification reagent 125 can be combined with a protein of interest under conditions where it can bind to the protein of interest. Thereafter, conditions can be adjusted such that polypeptide purification reagent 125 can bind to itself via its self-binding domain 127, thus forming precipitable polymers. FIG. 12B shows formation of such precipitable polymers in which the self-binding domain 127 binds to an identical domain on a different molecule of the polypeptide purification reagent 125, and a protein of interest is not bound to the polypeptide purification reagent 125. Such precipitable polymers may also be formed with a protein of interest bound to the polypeptide purification reagent 125, as just described. Moreover, the self-binding domain 127 may, but need not, bind to itself; it may bind to another portion of the polypeptide purification reagent 125.

As discussed above, a first precipitation can also be accomplished by aggregate formation, which also does not depend on the protein of interest being multimeric. One or more molecules, cells, viruses, or portions thereof, to which the CRD 107 of polypeptide purification reagent 117, 120, 121, 122, or 123 can specifically and reversibly bind can be added under conditions in which the CRD 107 can bind to the molecule, cell, or virus, or portion thereof and the polypeptide purification reagent can bind to the protein of interest. The skilled artisan will realize that such conditions include at least about 0.2 millimolar calcium. See e.g. Ogasawara and Voelker (1995), J. Biol. Chem. 270(32): 19052–19058. Examples of such molecules, viruses, or cells include glucan, influenza virus, *Escherichia coli, Cryptococcus neoformans, Aspergillus fumigatus*, and *Saccharomyces cerevisiae*. The resulting aggregated molecules can form a precipitate, comprising the protein of interest and the protein purification reagent.

The first precipitate can be separated from the solution by any suitable means, including filtration or centrifugation. After resuspension, optionally, the protein of interest can be further purified by reprecipitating the polypeptide purification reagent with the protein of interest bound to it one or more times, preferably by a different method from the previous precipitation(s). This reprecipitation can be accomplished by any of the methods discussed above.

The final precipitate, comprising a polypeptide purification reagent 111, 117, 120–123, or 125 and the protein of interest, can be resuspended under conditions in which the binding domain 115 cannot bind to the protein of interest and the polypeptide purification reagent cannot form a precipitate. As discussed above, one of skill in the art will realize what such conditions might be, depending on what the polypeptide purification reagent and the protein of interest are. The protein of interest can be separated from the polypeptide purification reagent 111, 117, 120–123,125 by any suitable means, including reprecipitation, affinity chromatography, or a separation based on differences in size, charge, or hydrophobicity between the protein of interest and the polypeptide purification reagent, as discussed above.

To separate the polypeptide purification reagent from the protein of interest, optionally, for polypeptide purification reagents comprising a functional CRD, such as 117, 120, 121, 122, and 123 (FIGS. 6B, 7A, 7B, 7C, and 8), a molecule, cell, virus, or portion thereof, to which the CRD 107 can bind, can be added under conditions in which the polypeptide purification reagent cannot bind to protein of interest but the CRD 107 can bind to its ligands. Examples of molecules, viruses, or bacteria that can be bound by C-type lectins include glucan, influenza virus, *Escherichia coli, Cryptococcus neoformans, Aspergillus fumigatus*, and *Saccharomyces cerevisiae*. See e.g. Brown-Augsburger et al. (1996), J. Biol. Chem. 271(31):18912–18919; Allen et al. (2001), Infection and Immunity 69(4):2037–2044; Lawson and Reid (2000), Immunological Reviews 173:66–78. If necessary, conditions can be adjusted such that the CRD 107 can bind to the molecule, virus, cell, or portion thereof. Such binding can be achieved in the presence of at least about 0.2 mM calcium. The resulting aggregate can form a precipitate comprising the polypeptide purification reagent but not the protein of interest, thus separating the protein of interest from the polypeptide purification reagent. Such a precipitate, comprising the polypeptide purification reagent, can be separated from the solution, comprising the protein of interest, by any appropriate means, including centrifugation or filtration.

As another way to separate the polypeptide purification reagent from the protein of interest, conditions can be adjusted such that the polypeptide purification reagent (not bound to the protein of interest) can form a precipitate resulting from crystal formation, PEG precipitation, self-binding (for polypeptide purification reagent 125 as shown in FIG. 12B), or salting out. As discussed above, such conditions may include altering the pH or adding of various concentrations of PEG or various salts. Such a precipitate, comprising the polypeptide purification reagent, can be separated from the solution, comprising the protein of interest, by any appropriate means, including centrifugation or filtration.

The invention also encompasses an essentially purified form of the protein of interest further comprising a detectable amount of a polypeptide purification reagent, as discussed herein.

The foregoing description of the specific embodiments reveals the general nature of the invention so that others can readily modify and/or adapt such embodiments for various applications without departing from the generic concepts presented herein. Any such adaptions or modifications are intended to be embraced within the meaning and range of equivalents of the disclosed embodiments. Phraseology and terminology employed herein are for the purpose of description and not of limitation. All references cited herein are incorporated by reference in their entirety.

What is claimed is:

1. A method for purifying a protein of interest comprising:
    (a) combining an isolated recombinant, non-antibody polypeptide purification reagent with the protein of interest, wherein all or part of the polypeptide purification reagent is the product of an in vitro selection for binding to the protein of interest;
    (b) adjusting conditions such that the polypeptide purification reagent can bind to the protein of interest and such that the polypeptide purification reagent, when bound to the protein of interest forms a precipitate; and
    (c) recovering the polypeptide purification reagent bound to the protein of interest as a precipitate,
    wherein the performance of steps (a)–(c) purifies the protein of interest.

2. The method of claim 1, further comprising the following steps:
    (d) re-suspending the precipitate under conditions such that the protein of interest does not bind to the polypeptide purification reagent and the polypeptide purification reagent does not form a precipitate; and
    (e) separating the protein of interest from the polypeptide purification reagent by affinity chromatography using an affinity reagent that specifically binds to the polypeptide purification reagent.

3. The method of claim 1, further comprising the following steps:
    (d) resuspending the precipitate under conditions such that the protein of interest does not bind to the polypeptide purification reagent and the polypeptide purification reagent does not form a precipitate;
    (e) adjusting the conditions such that the polypeptide purification reagent forms a precipitate and the protein of interest does not bind to the polypeptide purification reagent; and
    (f) separating the precipitate from the solution.

4. The method of claim 1, wherein the protein of interest comprises an $F_C$ portion of an antibody.

5. The method of claim 1, wherein the polypeptide purification reagent comprises at least two binding domains.

6. The method of claim 1, wherein the polypeptide purification reagent comprises part or all of a C-type lectin.

7. The method of claim 1, wherein the precipitate is a crystal.

8. The method of claim 1, wherein the precipitate is not a crystal.

9. The method of claim 8, wherein one molecule of the polypeptide purification reagent can bind to another molecule of the polypeptide purification reagent.

10. The method of claim 8, wherein the polypeptide purification reagent comprises at least two binding domains.

11. The method of claim 10, wherein at least two of the binding domains each bind to different epitopes on the protein of interest.

12. A method for purifying a protein of interest comprising:
    (a) combining a recombinant, non-antibody polypeptide purification reagent with the protein of interest under conditions such that a precipitate lacking a regular, crystalline structure comprising the polypeptide purification reagent and the protein of interest is formed; and
    (b) recovering the polypeptide purification reagent bound to the protein of interest as a precipitate
    wherein the performance of steps (a) and (b) purifies the protein of interest.

13. The method of claim 12, further comprising:
    (c) resuspending the precipitate under conditions such that the polypeptide purification reagent does not bind to the protein of interest;
    (d) separating the polypeptide purification reagent from the protein of interest; and
    (e) recovering both the polypeptide purification reagent and the protein of interest.

14. The method of claim 12, wherein the protein of interest comprises an $F_C$ portion of an antibody.

15. The method of claim 14, wherein the polypeptide purification reagent comprises at least two binding domains that can bind to an $F_C$ portion of an antibody.

16. The method of claim 15, wherein at least two of the binding domains comprise all or part of Protein A.

17. A method of purifying a protein of interest comprising:
(a) combining a recombinant, non-antibody polypeptide purification reagent with the protein of interest, wherein the polypeptide purification reagent comprises a binding domain and a distinct scaffold domain, wherein the scaffold domain comprises an amino acid sequence conferring a propensity to form a precipitate;
(b) adjusting conditions such that the polypeptide purification reagent can bind to the protein of interest and such that the polypeptide purification reagent, when bound to the protein of interest, can form a precipitate; and
(c) recovering the polypeptide purification reagent bound to the protein of interest as a precipitate
wherein the performance of steps (a)–(c) purifies the protein of interest.

18. The method of claim 17, wherein the protein of interest comprises all or part of antibody or a substantially similar protein.

19. The method of claim 17, wherein a binding domain in the polypeptide purification reagent has been selected in vitro to bind to the protein of interest.

20. The method of claim 17, wherein the polypeptide purification reagent comprises at least 2 binding domains.

21. The method of claim 20, wherein at least 2 binding domains comprise all or part of Protein A.

22. The method of claim 17, wherein plural molecules of the polypeptide purification reagent can bind to the scaffold domains of other molecules of the polypeptide purification reagent, thereby forming a precipitable polymer.

23. The method of claim 17, further comprising:
resuspending the precipitate under conditions such that the polypeptide purification reagent does not bind to the protein of interest and does not form a precipitate;
adjusting the conditions such that the polypeptide purification reagent does not bind to the protein of interest and does form a precipitate; and
separating the precipitate from the solution.

24. The method of claim 12, wherein the recombinant, non-antibody polypeptide purification reagent comprises at least one scaffold domain comprising all or part of a C type lectin and at least one binding domain.

* * * * *